(12) United States Patent
Vasudevan et al.

(10) Patent No.: US 11,931,374 B2
(45) Date of Patent: Mar. 19, 2024

(54) ADENOSINE RECEPTOR MODULATORS FOR THE TREATMENT OF CIRCADIAN RHYTHM DISORDERS

(71) Applicant: OXFORD UNIVERSITY INNOVATION LIMITED, Oxford (GB)

(72) Inventors: Sridhar Vasudevan, Oxford (GB); Aarti Jagannath, Oxford (GB); Russell Foster, Oxford (GB)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 0 days.

(21) Appl. No.: 16/912,143

(22) Filed: Jun. 25, 2020

(65) Prior Publication Data

US 2021/0106605 A1 Apr. 15, 2021

Related U.S. Application Data

(63) Continuation of application No. 15/573,963, filed as application No. PCT/GB2017/051029 on Apr. 12, 2017, now abandoned.

(30) Foreign Application Priority Data

Apr. 15, 2016 (GB) .................................... 1606622

(51) Int. Cl.
| | | |
|---|---|---|
| *A61K 31/53* | (2006.01) | |
| *A61K 31/44* | (2006.01) | |
| *A61K 31/4418* | (2006.01) | |
| *A61K 31/4439* | (2006.01) | |
| *A61K 31/505* | (2006.01) | |
| *A61K 31/517* | (2006.01) | |
| *A61K 31/519* | (2006.01) | |
| *A61K 31/522* | (2006.01) | |
| *A61K 31/5377* | (2006.01) | |
| *A61K 31/7076* | (2006.01) | |
| *A61P 25/00* | (2006.01) | |

(52) U.S. Cl.
CPC .......... *A61K 31/7076* (2013.01); *A61K 31/44* (2013.01); *A61K 31/4418* (2013.01); *A61K 31/4439* (2013.01); *A61K 31/505* (2013.01); *A61K 31/517* (2013.01); *A61K 31/519* (2013.01); *A61K 31/522* (2013.01); *A61K 31/53* (2013.01); *A61K 31/5377* (2013.01); *A61P 25/00* (2018.01)

(58) Field of Classification Search
CPC .................................................... A61K 31/52
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 7,230,102 B2 | 6/2007 | Giorgio et al. |
| 2006/0154268 A1 | 7/2006 | Yamamoto et al. |
| 2019/0111069 A1 | 4/2019 | Vasudevan et al. |

FOREIGN PATENT DOCUMENTS

| | | |
|---|---|---|
| DE | 3218121 | 11/1983 |
| EP | 0036676 A1 | 9/1981 |
| EP | 0052322 A2 | 5/1982 |
| EP | 0088046 A2 | 2/1983 |
| EP | 0102324 | 3/1984 |
| EP | 0142641 A2 | 5/1985 |
| EP | 0143949 A1 | 6/1985 |
| EP | 133988 | 8/2007 |
| EP | 1921077 A1 | 5/2008 |
| EP | 3280414 | 2/2018 |
| JP | 607934 A | 1/1985 |
| WO | 1997/041833 | 11/1997 |
| WO | 1999/016419 | 4/1999 |
| WO | 2001/085136 A2 | 11/2001 |
| WO | 2003032912 A2 | 4/2003 |
| WO | 2003/053411 A1 | 7/2003 |
| WO | 2007030438 A2 | 3/2007 |
| WO | 2008116185 A2 | 9/2008 |

(Continued)

OTHER PUBLICATIONS

St. Hilaire, M. A., Sleep Medicine, "Caffeine does not entrain the circadian clock but improves daytime alertness in blind patients with non-24-hour rhythms", 2015, vol. 16, pp. 800-804 (Year: 2015).*
Pinna, A. et al., Expert Opinion on Investigational Drugs, "Novel investigational adenosine A2A receptor antagonists for Parkinson's disease", 2009, vol. 18, No. 11, pp. 1619-1631 (Year: 2009).*
Videnovic, A. et al., Experimental Neurology, "Circadian and sleep disorders in Parkinson's disease", 2013, vol. 243, pp. 45-56 (Year: 2013).*
Atack, et al. "JNJ-40255293, a Novel Adenosine A 2A / A 1 Antagonist with Efficacy in Preclinical Models of Parkinson's Disease" ACS Chemical Neuroscience, vol. 5, No. 10, Oct. 15, 2014, pp. 1005-1019.
Emens, et al. "Non-24-Hour Disorder in Blind Individuals Revisited: Variability and the Influence of Environmental Time Cues." Sleep 36.7 (2013): 1091-1100. PMC. Web. Apr. 7, 2017.

(Continued)

*Primary Examiner* — Bahar Craigo
(74) *Attorney, Agent, or Firm* — Edwin S. Flores; Daniel J. Chalker; Chalker Flores, LLp

(57) ABSTRACT

The present invention relates to the use of adenosine receptor modulators to affect the circadian rhythm, in particular, to the use of such modulators for the treatment of circadian rhythm disorders. In particular, the invention relates to a composition comprising at least one selective adenosine receptor modulator, wherein said composition modulates two or three, but not all of adenosine receptor subtypes $A_1$, $A_{2A}$, $A_{2B}$ and/or $A_3$ for use in the treatment of circadian rhythm disorders or for modulating a biological clock.

11 Claims, 16 Drawing Sheets

Specification includes a Sequence Listing.

(56) References Cited

FOREIGN PATENT DOCUMENTS

| WO | 2012038980 A2 | 3/2012 |
|----|---------------|--------|
| WO | 2012066330 A1 | 5/2012 |
| WO | 2017178820 A1 | 10/2017 |

OTHER PUBLICATIONS

European Patent Office, International Search Report and Written Opinion for PCT/GB2017/051029 dated Jul. 7, 2017, 14 pp.

Hester, et al. "Caffiene increases light responsiveness of mouse circadian pacemaker" European Journal of Neuroscience, vol. 40, No. 10—pp. 3504-3511.

Jagannath, et al., "The CRTC1-SIK1 pathway regulates entrainment of the circadian clock" Cell. Aug. 29, 2013;154(5):1100-11.

Lévi, et al."Circadian timing in cancer treatments" Annu Rev Pharmacol Toxicol, first published online Nov. 17, 2009, 2010; 50:377-421.

Marcheva, et al. "Disruption of the clock components CLOCK and BMAL 1 leads to hypoinsulinaemia and diabetes" Nature, 466, 627-631, Jul. 2010.

Ortiz-Tudela, et al."The circadian rest-activity rhythm, a potential safety pharmacology endpoint of cancer chemotherapy" Int. J Cancer. Jun. 1, 2014;134(11):2717-25.

Peirson, et al., "Experimental validation of novel and conventional approaches to quantitative real-time PCR data analysis" Nucleic Acids Res. Jul. 15, 2003;31(14):e73.

Ruby, et al. "Adenosinergic Regulation of Striatal Clock Gene Expression and Ethanol Intake During Constant Light" Neuropsychopharmacology, vol. 39, No. 10, Apr. 23, 2014, pp. 2432-2440.

Schwart, et al., "Distinct patterns of Period gene expression in the suprachiasmatic nucleus underlie circadian clock photoentrainment by advances or delays" Proc Natl Acad Sci U S A 108, 17219-17224, published onlin Oct. 3, 2011.

Van Diepen, et al. "Caffeine increases light responsiveness of the mouse circadian pacemaker" European Journal of Neuroscience, vol. 40, accepted Aug. 5, 2014, pp. 3504-3511.

Yoo, et al., "PERIOD2::LUCIFERASE real-time reporting of circadian dynamics reveals persistent circadian oscillations in mouse peripheral tissues" Proc Natl Acad Sci U S A. Apr. 13, 2004;101(15):5339-46.

Zee, et al., 2013, Circadian rhythm abnormalities. Continuum: Lifelong Learning in Neurology, 19(1, Sleep Disorders), 132-147).

\* cited by examiner

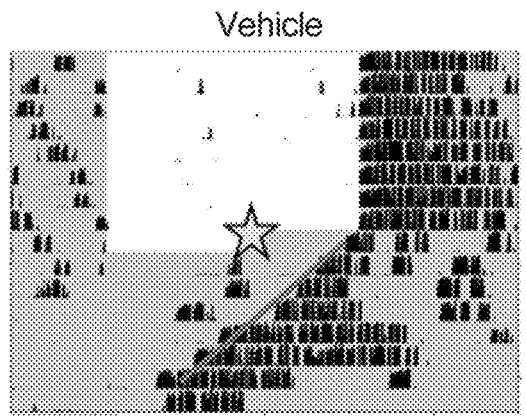
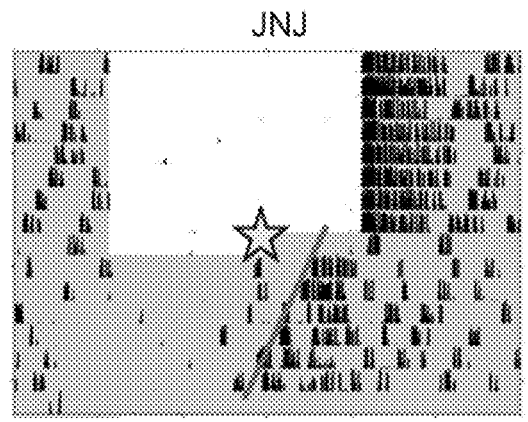
FIG. 4A    FIG. 4B
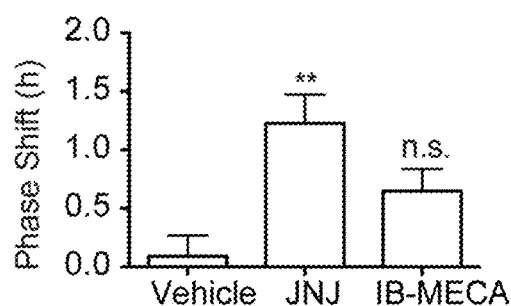
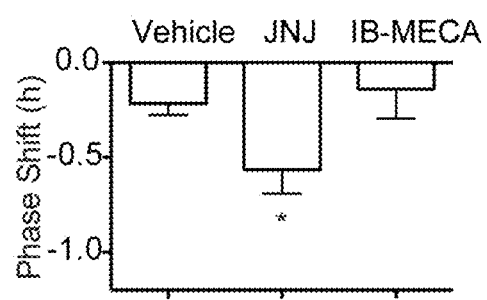
FIG. 4C    FIG. 4D
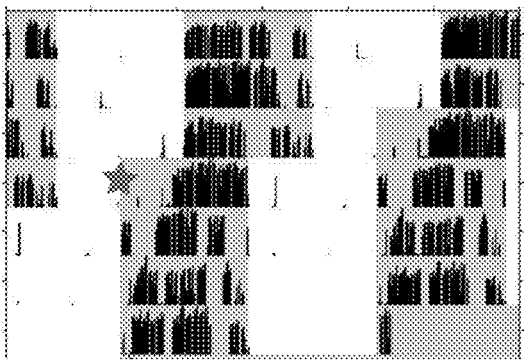
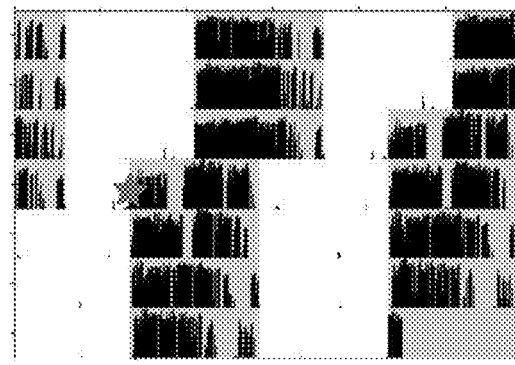
FIG. 4E    FIG. 4F

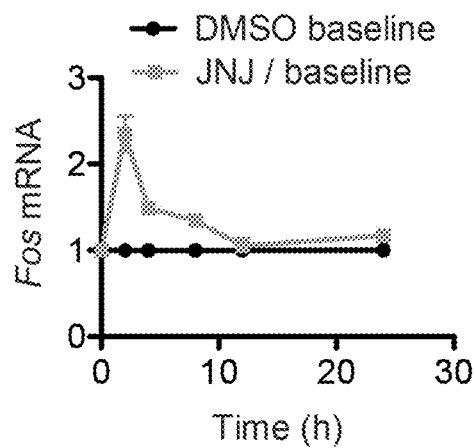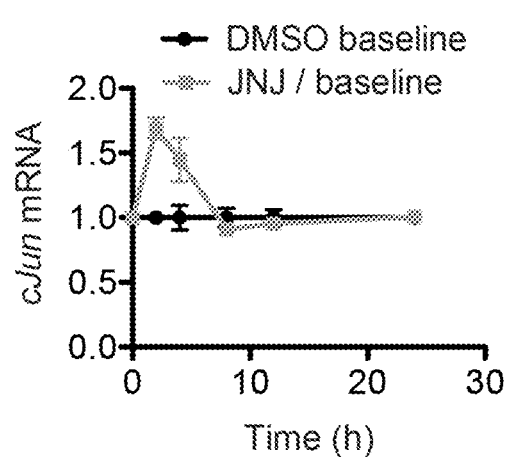
FIG. 7A          FIG. 7B
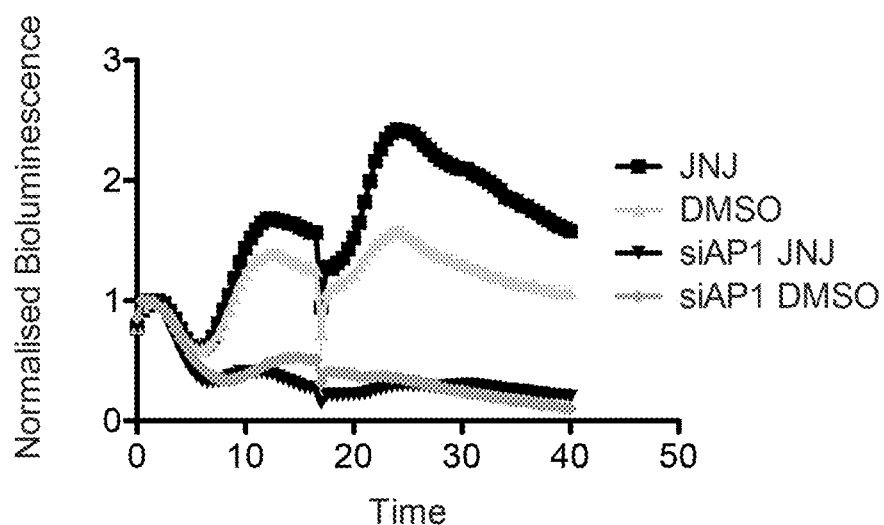
FIG. 7C

ADENOSINE RECEPTOR MODULATORS FOR THE TREATMENT OF CIRCADIAN RHYTHM DISORDERS

CROSS-REFERENCE TO RELATED APPLICATIONS

This application is continuation of U.S. patent application Ser. No. 15/573,963, filed Nov. 14, 2017, and which claims priority to International Application No. PCT/GB2017/051029, filed Apr. 12, 2017, which claims the priority of GB 1606622.7, filed Apr. 15, 2016. The contents of each of which are incorporated by reference in their entirety.

INCORPORATION-BY-REFERENCE OF MATERIALS

The present application includes a Sequence Listing which has been submitted in ASCII format via EFS-Web and is hereby incorporated by reference in its entirety. Said ASCII copy, created on Dec. 20, 2018, is named JA82877P.USP_SL.txt and is 2.62 kilobytes in size.

The present invention relates to the use of adenosine receptor modulators to affect the circadian rhythm, in particular, to the use of such modulators for the treatment of circadian rhythm disorders. In particular, the invention relates to a composition comprising at least one selective adenosine receptor modulator, wherein said composition modulates two or three, but not all of adenosine receptor subtypes $A_1$, $A_{2A}$, $A_{2B}$ and/or $A_3$ for use in the treatment of circadian rhythm disorders or for modulating a biological clock.

Almost all organisms on Earth apply an internal biological timer to anticipate changes that accompany the daily solar cycle. The possession of such an internal timer allows organisms to inherently "know" where in the daily solar cycle they are, absent of external cues. Such internally generated daily rhythms are called "circadian rhythms", and are endogenous to the organism.

The mechanisms underlying circadian rhythms involve circadian oscillations in processes such as gene expression and protein modifications. A core clock controls these circadian oscillations by signal generation.

The mammalian circadian clock in the brain conveys 24-hour rhythmicity to rest-activity cycles, temperature, sleep, and virtually all other behavioural and physiological processes. The imposition of an internal temporal framework is an essential part of an organism's biology; it allows all of the internal processes to work in harmony, such as gene expression, cell division and metabolism. In order for such rhythms to be adaptive, they must be synchronised, or entrained, to the external environment, predominantly produced by the 24 hour light/dark cycle due to the rotation of the Earth, and/or to other entraining signals, known as "time givers" or zeitgebers.

It is key that circadian rhythms are generated internally by the organism, and are not driven by the external environment. However, these endogenous circadian rhythms are adjusted by environmental signals, such that they are synchronised to the external cycle or clock.

In the absence of external cues or signals, the endogenous circadian rhythm in a human on average runs slightly longer than 24 hours. This may be the case in totally blind subjects who are lacking conscious light perception, where the complete absence of detection of the light/dark cycle may be sufficient for the clock to run free of adjustment based on external signals. In these cases, the circadian rhythm may require realignment, such that the internal clock is running at the same time as the external one.

The internal circadian clock has its own time, known as circadian time (CT); which is a standard of time based on the free-running period of a rhythm (oscillation). This may or may not be aligned with the external/environmental time. CT is effectively the internal time (either for the whole clock or the relevant tissue). Time relative to the external environment is denoted as ZT or Zeitgeber time. Under entrained conditions, CT0=ZT0=start of the light phase (typically 6 or 7 am) and under free-running conditions, CT0 in a human would be the time at which the onset of activity occurs. Determining the CT of a tissue or individual is possible via testing, as discussed later.

The mechanism underlying the clock is a ubiquitous cell autonomous transcription-translation feedback loop (TTFL) in which the transcription factors CLOCK and BMAL1 drive the expression of Period (Per1/2) and Cryptochrome (Cry1/2), whose protein products in turn feedback to inhibit CLOCK and BMAL1 resulting in a negative feedback loop within a 24 hour period.

Each individual cell of an organism has an individual cellular clock. Individual cellular clocks are maintained in synchrony by a master pacemaker in the suprachiasmatic nuclei (SCN) in the hypothalamus. In order to adapt to the external 24 hour world, the clock must receive and respond to signals that provide temporal cues (zeitgebers). Zeitgebers modulate the temporal expression pattern of clock genes such as Per1/2 (Schwartz et al., Proc Natl Acad Sci USA 108, 17219-17224, 2011) to set the phase, amplitude and period of oscillation of the molecular clock. Light, which signals the dawn-dusk cycle, drives cAMP response element binding factor (CREB)-mediated transcription of Per genes. However, circadian clocks throughout the body receive inputs from numerous sources including food, glucocorticoids and temperature. The molecular clock receives environmental input through ligands that bind to cell-surface and nuclear receptors and activate downstream signalling pathways that converge on the TTFL. While a few of these pathways are known (e.g. NMDA receptors signal light input to the SCN), the majority remain unknown.

It is possible for cells and/or tissues of the body to have a circadian rhythm that has de-synchronised with the central or SCN rhythm. In this scenario, the cells and/or tissues are running with a different rhythm to the rest of the body. This can result in pathologies developing in those cells and tissues, since inappropriately timed physiological processes are undertaken.

For example, it has been shown that a "faulty" or mis-aligned circadian clock in pancreatic tissues may be related to the development of diabetes. (Disruption of the clock components CLOCK and BMAL1 leads to hypoinsulinaemia and diabetes, Marcheva et al, Nature, 466, 627-631, July 2010).

When an internal de-synchrony occurs between a person's biological clock and their environmental 24-hour schedule, a group of pathologies known as circadian rhythm disorders can occur. This de-synchronisation can occur in the SCN, and thus the circadian rhythm of the whole body, or can occur in selected tissues peripheral to the SCN as described above. It is possible for either central or peripheral de-synchronisation to occur without any manifest symptoms. Where the circadian rhythm of a subject is not synchronised to the external/environmental clock, it can be said to be free-running. Ultimately, since a free-running clock can be up to one hour longer than the external clock in illustration, every 12 days, the subject's circadian rhythm will be completely antiphase to the outside world, and will experience extreme jet-lag symptoms.

Where the circadian rhythm and the external/environmental clock are de-synchronised, this can have many physiological and behavioural impacts. Several circadian rhythm dysfunctions may result from the lack of synchrony with the external clock.

In some instances, de-synchronisation of a person's SCN circadian rhythm may be detected since the rest-activity rhythm changes. The timings of rest and activity can be measured using an actimetry sensor, for example. A correlation has been shown between the non-entrained drift in the circadian phase and the non-24-h component of the rest-activity rhythm in subjects when wrist actigraphy data analysed. There is a possibility that chronic circadian misalignment could also result in adverse metabolic, cognitive, and emotional consequences in subjects with Non-24 disorder (Emens, Jonathan S. et al. "Non-24-Hour Disorder in Blind Individuals Revisited: Variability and the Influence of Environmental Time Cues." Sleep 36.7 (2013): 1091-1100. PMC. Web. 7 Apr. 2017).

Circadian rhythm misalignment or dysfunctions may be introduced into an individual, such as through pharmacological intervention. For example, it has been shown that some cancer treatments are capable of altering the circadian rhythm (Ortiz-Tudela E., et al, Int. J Cancer. 2014 Jun. 1; 134(11):2717-25.) Such dysfunctions in the circadian rhythm may be correlated with poorer outcomes for treatment, and thus it is important that these are recognised and addressed. In converse, it is also known that some proteins targeted by pharmacological agents are expressed only during certain times of day and this may be out of the patient's wake time (e.g. 3 am). Under this circumstance it would be of use to alter the circadian rhythms to align the "drug-time" to the wake time.

Circadian rhythm misalignment may also occur when individuals travel across time zones. Jet lag, also described as desynchronosis and circadian dysrhythmia, is a physiological condition which results from rapid long-distance trans-meridian (east-west or west-east) travel.

Further, circadian rhythm misalignment may occur for shift workers, who are working in the evening and overnight, since they are active during their normal rest cycle. Shift work disorder is a recognised circadian rhythm disorder.

Certain circadian rhythm disorders may be circadian rhythm sleep disorders, where the misalignment of the circadian clock manifests in the timing of sleep, which itself is determined from the rest-activity rhythm.

Current methods of treatment of circadian rhythm disorders primarily centre around bright light therapy and the use of melatonin receptor agonists. These methods have their drawbacks; they are not uniformly effective, for example, melatonin has not been shown to have any effect in Advanced Sleep Phase Syndrome or jet-lag in westward travel, and mixed outcomes are observed with Shift Work Disorder and non-24 h sleep disorders. Bright light therapy requires exposure to high levels of light (2,500-10,000 lux) at precise time windows each day (reviewed in Zee et al., 2013, Circadian rhythm abnormalities. Continuum: Lifelong Learning in Neurology, 19(1, Sleep Disorders), 132-147) and for the subject to be sighted.

The present invention uses the adenosine signalling pathway, a novel and uncharacterized clock-regulatory pathway, as a target for therapeutic purposes. More particularly, the present invention takes advantage of modulating at least two adenosine receptors, to utilise the adenosine signalling pathway to alter and/or realign the circadian rhythm of an individual. The present inventors have realised that to be physiologically relevant and also tolerable to the subject, treatment to move or shift a circadian rhythm (for whatever reason) requires the modification of at least two adenosine receptor subtypes. This is desirable; since it would appear that different adenosine receptor subtypes may modulate the circadian rhythm via different pathways, and that the cumulative effect is much more promising than single receptor modulation. The results included here demonstrate that at least the $A_1$ receptor and the $A_{2A}$ receptor utilise different signalling pathways, and that the combination of modulators at these receptors selectively is advantageous in modifying, shifting or moving the circadian clock or rhythm of an individual. It can been seen from the Figures and Examples that it is only possible to induce Per1 and Per2 expression by targeting two adenosine receptor subtypes, in the examples these are the $A_1$ receptor and the $A_{2A}$ receptor. As used herein, adenosine receptors and adenosine receptor subtypes refer to the $A_1$, $A_{2A}$, $A_{2B}$ and/or $A_3$ receptors or receptor subtypes.

Modifying a sole adenosine receptor subtype using a sole experimental therapeutic is not desirable, since it has a less potent effect on the circadian clock, and is furthermore associated with more risk of serious side effects from the treatment. For example, clinical trials for the use of selective $A_1$ receptor antagonists have been halted due to the subjects suffering seizures. Therefore, the use of $A_1$ receptor antagonists to modify the circadian rhythm would be considered by those in the art to be contra-indicated by the risk of serious side effects, and thus the use of these would not be therapeutically relevant. Moreover, it is also not therapeutically relevant to modify all of the adenosine receptor subytpes. Modifying all of the subtypes leads to unwanted side effects, since adenosine receptors are so ubiquitously expressed throughout different tissues and may have many physiological roles. Therefore, the use of caffeine, which antagonises all types of adenosine receptors (ARs): $A_1$, $A_{2A}$, $A_3$, and $A_{2B}$, and similar compounds falls outside the scope of this invention. Many of the earliest adenosine receptor modulators developed also would modulate all of the receptor subtypes. Such compounds include CGS 15943. This latter compound can bind to all four adenosine receptors[3]. As such, this compound falls outside of the scope of the present invention.

According to a first aspect the invention provides an adenosine receptor modulator for use in the treatment of circadian rhythm disorders.

BRIEF DESCRIPTION OF THE DRAWINGS

For a more complete understanding of the present disclosure and the advantages thereof, reference is now made to the following brief description, taken in connection with the accompanying drawings and detailed description:

FIG. 3I is STAR-PROM screening that was conducted and nucleic acid signatures switched on by JNJ40255293s. FIG. 3J is a graph that demonstrates that Per1 mRNA levels are elevated after JNJ40255293 application in U2OS cells as measured by qPCR. FIG. 3K is a graph which demonstrates Per2 mRNA levels are elevated after JNJ40255293 application in U2OS cells as measured by qPCR.

FIGS. 4A-4B demonstrates a control animal released from entrained conditions to free-run and JNJ40255293 treated animal (star) in an identical set up as FIG. 4A.

FIGS. 4C and 4D are graphs. FIG. 4C—demonstrates the phase shift induced by administration of the indicated drug (IB-MECA 1 mg/kg, JNJ40255293 5 mg/kg and CGS15943 5 mg/kg) at time ZT6. FIG. 4D—demonstrates the phase shift induced by administration of the indicated drug (IB-MECA 1 mg/kg, JNJ40255293 5 mg/kg and CGS15943 5 mg/kg) at time CT16.

FIG. 4E shows re-entrainment in a jet-lag protocol in a control vehicle-treated animal, and FIG. 4F shows re-entrainment in a jet-lag protocol in a JNJ40255293 (5 mg/kg) treated animal.

FIG. 4G—demonstrates the dose response curve for re-entrainment in a jet-lag protocol, JNJ40255293 dose responsively enhanced re-entrainment. FIG. 4H—demonstrates that Per1 mRNA levels are elevated within the SCN after JNJ40255293 administration in the periphery (intra-peritoneally). FIG. 4I—demonstrates that Per2 mRNA levels are elevated within the SCN after JNJ40255293 administration in the periphery (intra-peritoneally). FIG. 4J—shows the Per2::Luc rhythms from SCN explants from Per2::Luc transgenic animals. JNJ40255293 (10 uM) added at the arrow. FIG. 4K—demonstrates the administration of 5 mg/kg JNJ40255293 and onsets of activity measured.

FIGS. 7A-7C are graphs which show that the STAR-PROM approach reveals a novel signaling pathway downstream of adenosine receptor inhibition that converges on the circadian clock.

FIG. 10B is a series of individual actograms which support the data shown in FIGS. 5A to 5H. The various agents applied to the animals are labelled.

Figure 1A:
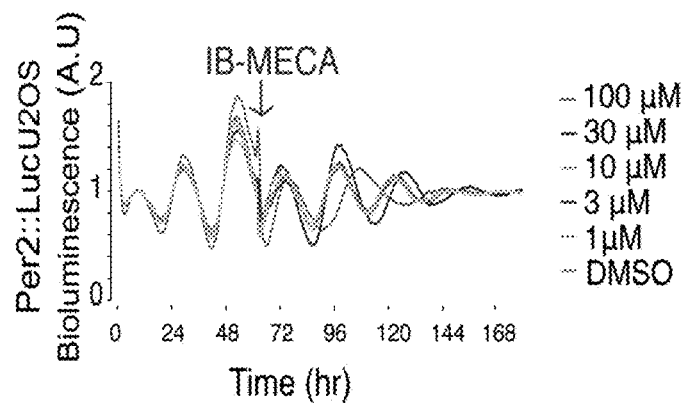
FIGS. 1A-1M are graphs which demonstrate that adenosine receptor agonists activate clock gene expression in U2OS cells.

An adenosine receptor modulator refers to a modulator which acts as an agonist, inverse agonist or an antagonist of the adenosine receptor. The modulator is preferably an antagonist or inverse agonist.

An 'adenosine receptor' is a class of purigenic G protein-coupled receptors with adenosine as an endogenous ligand. These receptors are widely distributed throughout the body and are divided into four subclasses, which include $A_1$, $A_{2A}$, $A_{2B}$ and $A_3$ adenosine receptors. Adenosine functions as a signalling molecule through the activation of these four distinct adenosine receptors, which are widely expressed and have been implicated in several biological functions, both physiological and pathological. Adenosine receptors occur as four different subtypes of GPCRs, with the Gs coupled $A_{2A}$ and $A_{2B}$ receptor subtypes and the Gi coupled $A_1$ and $A_3$ receptor subtypes. Differential expression of these receptors can lead to very different downstream effects of adenosine signalling through diverse effectors.

The adenosine receptor targeted by the modulator or composition of the invention may be any adenosine receptor, present in any tissue. The adenosine receptor may be in the brain, most notably in the hypothalamus, and most particularly in the suprachiasmatic nucleus (SCN). The adenosine receptor may be in tissues peripheral to the brain. Tissue peripheral to the brain may include any cell type, tissue or organ which does not form part of the brain. These may be, without limitation: blood and immune system cells, bone marrow cells, epithelial or skin cells, germ cells, contractile and muscle cells, neurons, hormone-secreting cells and secretory cells. These may also be from muscle, epithelial, connective and nervous tissue types, more specifically tissue or organs from the cardiovascular system, lungs, heart, circulatory system, immune or lymphatic system, stomach, pancreas, liver, spleen, small or large intestine, reproductive tissues, kidneys, bladder or urinary system, muscle, bone marrow, skin, endocrine system or peripheral nervous system.

The modulator may have good affinity for the $A_1$, $A_{2A}$, $A_{2B}$ and/or $A_3$ adenosine receptors, but not all four receptor subtypes. Thus, the modulator will have affinity for and bind to two or three of the $A_1$, $A_{2A}$, $A_{2B}$ and/or $A_3$ adenosine receptors, but will not bind to all of them. Preferably, the modulator will have affinity for and bind to two of the receptor subtypes, and not have affinity or bind to the remaining two subtypes. The modulator may have affinity, preferably a good affinity for the $A_1$ receptor. The modulator may have affinity, preferably a good affinity for the $A_{2A}$ or $A_{2B}$ receptor. The modulator may have affinity, preferably a good affinity for the $A_{2A}$ receptor. The modulator may have affinity, preferably a good affinity for the $A_{2B}$ receptor. The modulator may have affinity, preferably a good affinity for the $A_3$ receptor. The modulator may have an affinity, preferably a good affinity for the $A_1$ receptor and any one or two of the $A_{2A}$, $A_{2B}$ and/or $A_3$ receptor subtypes. The modulator may have an affinity, preferably a good affinity for the $A_{2A}$ receptor and any one or two of the $A_1$, $A_{2B}$ and/or $A_3$ receptor subtypes. The modulator may have an affinity, preferably a good affinity for the $A_{2B}$ receptor and any one or two of the $A_1$, $A_{2A}$ and/or $A_3$ receptor subtypes. The modulator may have an affinity, preferably a good affinity for the $A_3$ receptor and any one or two of the $A_1$, $A_{2A}$ and/or $A_{2B}$ receptor subtypes. Affinity may be defined as the ability of the modulator to bind to the cognate receptor, and be measured using occupancy of the receptor. Good affinity for a receptor in this context means that above about 25% of the receptors are occupied by the modulator. A desirable affinity for the receptor may be in the region of 15%-90% receptor occupancy, 15% to 80% occupancy, 20% to 70% occupancy, preferably 20% to 50% occupancy or 20% to 40% occupancy. Affinity may further be defined as the probability of the modulator occupying the receptor at any given instant.

The modulator or selective modulator may bind to its cognate adenosine receptor via any appropriate mechanism, including allosterically or orthosterically.

The modulator is preferably a selective modulator. This modulator may be selective for one, two or three adenosine receptor subtypes, but does not have affinity for all four subtypes. A selective modulator is preferably selective for one or two adenosine receptor subtypes only. Thus, non-selective adenosine receptor modulators that modulate all of the receptor subtypes do not fall within the scope of this aspect of the invention.

In some embodiments, it is preferred that a composition is provided as the adenosine receptor modulator, said composition comprising at least one selective adenosine receptor modulator, wherein said composition modulates two or three, but not all of adenosine receptor subtypes $A_1$, $A_{2A}$, $A_{2B}$ and/or $A_3$. It is thus preferred to modulate two or three, but not all of adenosine receptor subtypes $A_1$, $A_{2A}$, $A_{2B}$ and/or $A_3$ in the uses and methods of the invention. Optionally, the composition comprises one or two selective adenosine receptor modulators that act at either one or two adenosine receptor subtypes. These selective adenosine receptor modulators do not have affinity for the other two receptor subtypes, and preferably do not bind or interact at all at these receptors.

In some embodiments, it is preferred that the composition modulates $A_1$ and $A_{2A}$ and/or $A_{2B}$ receptor subtypes. In another embodiment, the composition preferably modulates $A_1$ and $A_{2A}$ receptor subtypes. In any of these embodiments, it is preferred that none of the other adenosine receptor subtypes are modulated. The other receptor subtypes are those not specified or listed—i.e. for a specific modulation of the $A_1$ and $A_{2A}$ receptor subtypes, it is preferred that the $A_{2B}$ and/or $A_3$ receptor subtypes are not modulated. It is preferred that a composition or selective modulator binds only to the $A_1$ and $A_{2A}$ receptor subtypes and not to the $A_{2B}$ and/or $A_3$ receptor subtypes. Optionally, the composition can comprise one selective adenosine modulator that is selective for the $A_1$ and $A_{2A}$ receptor subtypes.

In some embodiments, the selective adenosine receptor modulator may have at least 20% affinity, or at least 30% affinity, or at least 40% affinity or at least 50% affinity or at least 60% affinity or at least 70% affinity or at least 80% affinity or at least 90% affinity or more for one, two or three of the $A_1$, $A_{2A}$, $A_{2B}$ and $A_3$ adenosine receptors, with the proviso that the selective adenosine receptor modulator or composition does not have affinity for all four receptor subtypes. It is preferred that the selective adenosine modulator has affinity for only two receptor subtypes, i.e. it is a dual antagonist or inverse agonist. The selective adenosine receptor modulator may have a unique or specific affinity for each of its cognate receptors. For example, a selective adenosine receptor modulator may have a 50% affinity for the $A_1$ adenosine receptor and a 55% affinity for the $A_{2A}$ adenosine receptor.

In one embodiment, the selective adenosine receptor modulator may have at least 20% affinity, or at least 30% affinity, or at least 40% affinity or at least 50% affinity or at least 60% affinity or at least 70% affinity or at least 80% affinity or at least 90% affinity or more for the $A_1$ adenosine receptor. The selective modulator may have a 25% affinity or more for the $A_1$ adenosine receptor. Preferably, the modulator has 50-70% affinity for the $A_1$ adenosine receptor. The use of a selective adenosine receptor modulator against the $A_1$ receptor alone does not fall within the scope of this invention. At least one other adenosine receptor must also be modified, either by the same compound, or by a combination of selective modulators.

In another embodiment, the selective adenosine receptor modulator may have at least 20% affinity, or at least 30% affinity, or at least 40% affinity or at least 50% affinity or at least 60% affinity or at least 70% affinity or at least 80% affinity or at least 90% affinity or more for the $A_{2A}$ receptor. Preferably, the adenosine receptor modulator has at least 30% affinity for the $A_{2A}$ adenosine receptor. The selective modulator may have a 25% affinity or more for the $A_{2A}$ adenosine receptor. Preferably, the modulator has 50-70% affinity for the $A_{2A}$ adenosine receptor. The use of a selective adenosine receptor modulator against the $A_{2A}$ receptor alone does not fall within the scope of this invention. At least one other adenosine receptor must also be modified, either by the same compound, or by a combination of selective modulators.

In another embodiment, the selective adenosine receptor modulator may have at least 20% affinity, or at least 30% affinity, or at least 40% affinity or at least 50% affinity or at least 60% affinity or at least 70% affinity or at least 80% affinity or at least 90% affinity or more for the $A_{2B}$ receptor. The selective modulator may have a 25% affinity or more for the $A_{2B}$ adenosine receptor. The selective adenosine receptor modulator may have at least 30% affinity for the $A_{2B}$ adenosine receptor. Preferably, the modulator has 50-70% affinity for the $A_{2B}$ adenosine receptor.

In yet another embodiment, the selective adenosine receptor modulator may have at least 20% affinity, or at least 30% affinity, or at least 40% affinity or at least 50% affinity or at least 60% affinity or at least 70% affinity or at least 80% affinity or at least 90% affinity or more for the $A_3$ adenosine receptor. The selective modulator may have a 25% affinity or more for the $A_3$ adenosine receptor. Preferably, the modulator has 50-70% affinity for the $A_3$ adenosine receptor.

In one aspect of the invention, there is provided a composition which comprises one or more selective adenosine receptor modulators ("selective modulator"). For example, the composition may comprise 1, 2 or 3 selective adenosine receptor modulators, preferably 2, each of which is specific for a particular adenosine receptor subtype. Each of the selective modulators can be defined as described above, and each may have a different affinity for their cognate receptor. One selective adenosine receptor modulator can be used in the composition that is selective for two adenosine receptor subtypes, in combination with a second selective adenosine receptor modulator that is selective for a third adenosine receptor subtype. Alternatively, three individual selective modulators could be used, each of which modulate a different adenosine receptor.

Affinity as used herein may correlate with receptor occupancy, such that an affinity of at least 20% would correlate with an occupancy of at least 20%, that is, at least 20% of the expressed receptor is occupied by the modulator. Receptor occupancy can be quantified by routine methods, including flow cytometry assays and radioligand binding assays. Occupancy of at least about 25% is desirable to indicate that the modulator has a good affinity to the receptor.

It is a preferred feature of the invention that some, but not all of the adenosine receptor subtypes are modified. Where it is desired that a particular or specified adenosine receptor subtype is not modified, that modulator or composition has limited or no affinity for that adenosine receptor subtype. This means that the adenosine receptor modulator or composition shows less than 10% affinity, preferably less than 9, 8, 7, 6, 5, 4, 3, 2 or 1% affinity for the specified adenosine receptor subtype. In a preferred embodiment, the adenosine receptor modulator or composition shows no affinity for the specified adenosine receptor subtype. The adenosine receptor modulator preferably does not bind to or interact with the specified receptor subtype. The "specified" receptor subtype can be identified by omission. For example, if a selective modulator is described as acting selectively at the $A_1$ and $A_{2A}$ adenosine receptors, then by its nature, it does not act at the $A_{2B}$ and $A_3$ adenosine receptors. The modulator of the invention may be a modulator of $A_{2A}$, $A_{2B}$ and/or $A_3$ adenosine receptors. It is preferred in this embodiment that the modulator is not a modulator of the $A_1$ adenosine receptor.

The selective modulator of the invention may be a modulator of $A_1$, $A_{2A}$ and/or $A_{2B}$ adenosine receptors. It is preferred in this embodiment that the selective modulator is not a modulator of the $A_3$ adenosine receptor.

The selective modulator of the invention may be a modulator of $A_1$ and $A_{2A}$ adenosine receptors. It is preferred in this embodiment that the selective modulator is not a modulator of the $A_{2B}$ or $A_3$ adenosine receptors.

In an aspect of the invention the modulator, selective modulator or composition is intended to modulate adenosine receptors in the brain, preferably in the hypothalamus, optionally in the SCN.

In another aspect of the invention, the modulator, selective modulator or composition is intended to modulate adenosine receptors in the lung. This may be used to manage or treat asthma.

In another aspect of the invention, it is intended to modulate adenosine receptors in the pancreas. This may be used to manage or treat diabetes.

In a further aspect of the invention, it is intended to modulate the adenosine receptors in a specific cell type, tissue type or organ. This may be any cell type, tissue type or organ. Exemplary cell types include but are not limited to: blood and immune system cells, bone marrow cells, epithelial or skin cells, germ cells, contractile and muscle cells, neurons, hormone-secreting cells and secretory cells. These may also be from muscle, epithelial, connective and nervous tissue types, more specifically tissue or organs from the cardiovascular system, lungs, heart, circulatory system, immune or lymphatic system, stomach, pancreas, liver, spleen, small or large intestine, reproductive tissues, kidneys, bladder or urinary system, muscle, bone marrow, skin, endocrine system or peripheral nervous system.

In one aspect, the invention provides a composition comprising at least one selective adenosine receptor modulator, wherein said composition modulates two or three, but not all of adenosine receptor subtypes $A_1$, $A_{2A}$, $A_{2B}$ and/or $A_3$ for use in the treatment of circadian rhythm disorders or for modulating a biological clock. Optionally, the composition is selective for $A_1$ and $A_{2A}$ adenosine receptors. It is preferred in this embodiment that the composition does not comprise a modulator of the $A_{2B}$ or $A_3$ adenosine receptors.

A selective adenosine receptor modulator is as described here previously. Similarly, a circadian rhythm disorder and modulation of a biological clock are as defined herein.

It may be desirable to modulate a biological clock, also known as a circadian clock, in situations where the individual's circadian rhythm is not otherwise disturbed. It has been found that the timings of some pharmacological interventions are important in relation to their effectiveness, as they may target a particular cellular function that occurs at that "circadian time: CT". For example, it has been found that CT 15 (10 pm if synchronised with the external clock) may be an effective time to administer certain chemotherapy drugs (Levi F et al, Circadian timing in cancer treatments. Annu Rev Pharmacol Toxicol. 2010; 50:377-421.) This is not a socially acceptable time for the patient or physician to be administering drugs. Therefore, it is possible to modulate their biological clock, such that it is put out of synchrony with the external clock. Thus, the administration of selective modulator or composition may be used to shift the biological clock to bring the effective CT time for treatment to a better external time.

Alternative reasons to modulate the biological clock may include international travel, preparation for shift work, or other social, non-health related reasons for wishing to modify the rest-activity cycles.

Thus, the present invention encompasses non-medical methods of treatment, such as a method of modulating a biological clock comprising the administration of a composition comprising at least one selective adenosine receptor modulator, wherein said composition modulates two or three, but not all of adenosine receptor subtypes $A_1$, $A_{2A}$, $A_{2B}$ and/or $A_3$. Optionally two adenosine receptor subtypes are modulated. Methods of medical treatment a method of modulating a biological clock or treating a circadian rhythm disorder or dysfunction, comprising the administration of a composition comprising at least one selective adenosine receptor modulator, wherein said composition modulates two or three, but not all of adenosine receptor subtypes $A_1$, $A_{2A}$, $A_{2B}$ and/or $A_3$ are also encompassed where allowable.

Further, the present invention includes a composition comprising at least one selective adenosine receptor modulator, wherein said composition modulates two or three, but not all of adenosine receptor subtypes $A_1$, $A_{2A}$, $A_{2B}$ and/or $A_3$ for use in circadian realignment. Optionally, the composition is selective for $A_1$ and $A_{2A}$ adenosine receptors. It is preferred in this embodiment that the composition does not comprise a modulator of the $A_{2B}$ or $A_3$ adenosine receptors.

Additionally, the present invention extends to a method of realignment of the circadian rhythm comprising the once a day administration of a compound comprising at least one selective adenosine receptor modulator, wherein said composition modulates two or three, but not all of adenosine receptor subtypes $A_1$, $A_{2A}$, $A_{2B}$ and/or $A_3$. Optionally, the composition is selective for $A_1$ and $A_{2A}$ adenosine receptors. It is preferred in this embodiment that the composition does not comprise a modulator of the $A_{2B}$ or $A_3$ adenosine receptors.

The present invention also includes a composition comprising at least one selective adenosine receptor modulator, wherein said composition modulates two or three but not all of adenosine receptor subtypes $A_1$, $A_{2A}$, $A_{2B}$ and/or $A_3$ for use in circadian realignment or adjustment by administration once a day. Optionally, the composition is selective for $A_1$ and $A_{2A}$ adenosine receptors. It is preferred in this embodiment that the composition does not comprise a modulator of the $A_{2B}$ or $A_3$ adenosine receptors.

It is preferred for all aspects and embodiments of the invention that the modulator, selective modulator or composition is administered once a day. This once a day administration sends a powerful signal to alter the circadian rhythm, and repeated administrations within a 24 hour period should not be necessary or desirable.

The timing of this single administration alters the circadian rhythm or clock profoundly.

In order to advance the circadian rhythm or biological clock of an individual (or a cell, tissue or organ thereof) according to any aspect or embodiment of the invention, it is preferred to administer the modulator, selective modulator or composition between about CT4 to 8, preferably between CT5 and 7, or at CT6. To "advance" the circadian rhythm means to bring the rhythm forwards in the external day.

In order to delay the circadian rhythm of an individual (or a cell, tissue or organ thereof) according to any aspect or embodiment of the invention, it is preferred to administer the modulator, selective modulator or composition between about CT14 to 18, preferably between CT15 and 17, or at CT16. To "delay" the circadian rhythm means to push the rhythm backwards in the external day.

The modulator, selective modulator or composition of the invention may result in an increase in Per1 gene expression after administration to a subject. Preferably the increase is observed at least 2 to 6 hours after administration, preferably at least 4 hours after administration. The increase in Per1 expression may be about 10%, about 20%, about 30%, about 40%, about 50%, about 60%, about 70%, about 80%, about 90%, about 100% or more increase in expression compared to in a subject without the administration of the modulator. The increase in Per1 expression may be determined at the RNA or the protein level.

The modulator, selective modulator or composition of the invention may result in an increase in Per2 gene expression after administration to a subject. Preferably the increase is observed at least 2 to 6 hours after administration, preferably at least 4 hours after administration. The increase in Per2 expression may be about 10%, about 20%, about 30%, about 40%, about 50%, about 60%, about 70%, about 80%, about 90%, about 100% or more increase in expression compared to in a subject without the administration of the modulator. The increase in Per2 expression may be determined at the RNA or the protein level.

An increase in both Per1 and Per2 gene expression may be observed, and is desirable.

In some embodiments, adenosine receptor modulators, selective modulators or compositions in accordance with the present invention may be used to treat, alleviate, ameliorate, relieve, delay onset of, inhibit progression of, reduce severity of, and/or reduce incidence of one or more symptoms or features of a circadian rhythm disorder.

In some embodiments, adenosine receptor modulators, selective modulators or compositions in accordance with the present invention may be used to treat, alleviate, ameliorate, relieve, delay onset of, inhibit progression of, reduce severity of, and/or reduce incidence of one or more symptoms or features of a circadian rhythm dysfunction.

In some embodiments, adenosine receptor modulators, selective modulator or composition in accordance with the present invention may be used for modulating a biological clock or circadian realignment. Modulation of the clock may occur when it is desired to take a circadian clock out of alignment with the current external clock, and realignment may be used to put it back into the correct alignment with the external clock. Either or both may be required when assisting the effective timing of pharmacological or other therapeutic interventions.

The circadian rhythm disorder may be a circadian rhythm sleep disorder, or a circadian rhythm dysfunction. The circadian rhythm sleep disorder may include, but is not limited to, jet-lag disorder or rapid time zone change syndrome, delayed sleep-phase disorder, advanced sleep-phase disorder, Irregular sleep wake rhythmic disorder, non-24-hour sleep wake disorder, shift-work disorder, or disruptive circadian rhythms. The circadian rhythm disorder may be non-24-hour sleep wake disorder in anophthalmic subjects. The circadian rhythm disorder may be shift-work disorder.

The circadian rhythm disorder may be jet-lag disorder. The circadian rhythm disorder may be advanced sleep phase disorder.

The circadian rhythm dysfunction may be any detected desynchronisation of the SCN circadian rhythm or individual peripheral tissue circadian rhythm, which are preferably not presenting as a circadian rhythm sleep disorder. It is possible to detect desynchronisation of a circadian rhythm with the external clock by various means. For example, an actimetry sensor or similar can be used to monitor periods of rest and activity. Other appropriate measurements can be hormone levels, blood pressure, heart rate and the like. For specific tissues, measurements of metabolites, hormone levels, gene expression or protein modification can give an indication of the circadian rhythm in that tissue, cells or organ. These tissues, cells and organs are as defined previously.

The adenosine receptor antagonist may be any agent that inhibits or antagonizes the adenosine receptor. Similarly an adenosine receptor agonist may be any agent that activates or acts as an agonist to the adenosine receptor. Such an antagonist or agonist may be a small molecule, a peptide, a protein, an RNA therapy, such as an siRNA, or an antibody or antibody fragment, particularly a monoclonal antibody. Preferably, the antagonist or agonist is a small molecule.

The selective adenosine receptor antagonist may be any agent that inhibits or antagonizes the specified adenosine receptor. Similarly a selective adenosine receptor inverse agonist may be any agent that acts at a constitutively active adenosine receptor to decrease the activity below the basal level of the adenosine receptor. The basal level of activity is measured in the absence of adenosine. Antagonists and inverse agonists can, therefore, have a similar effect to decrease the activity of the receptor in relation to the natural ligand, adenosine.

Such an antagonist, agonist or inverse agonist may be a small molecule, a peptide, a polypeptide, a protein, a non-coding RNA, such as a short hairpin RNA (shRNA), anti-sense RNA (asRNA), microRNA (miRNA), small interfering RNA (siRNA), trans-acting RNA (tasiRNA), antagomirs, aptamers, miRNA sponges, and any other functional RNA, or an antibody, antibody fragment or derivative of an antibody, particularly a monoclonal antibody. Preferably, the antagonist or inverse agonist is a small molecule.

The agonist, inverse agonist or antagonist may be a repurposed known molecule or a novel molecule. Exemplary adenosine receptor agonists and antagonists include:

1-Deoxy-1-[6-[((3-Iodophenyl)methyl)amino]-9H-purin-9-yl]-N-methyl-β-D-ribofuranuronamide, $N^6$-(3-Iodobenzyl)adenosine-5'-N-methyluronamide, also known as IB-Meca and is an $A_3$ adenosine receptor agonist

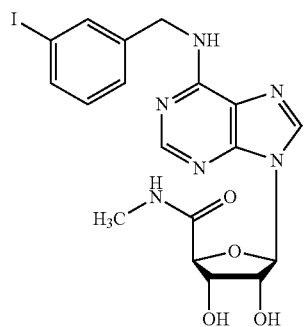

2-[[6-Amino-3,5-dicyano-4-[4-(cyclopropylmethoxy) phenyl]-2-pyridinyl]thio]-acetamide, also known as BAY-606583 and is an $A_{2B}$ receptor agonist

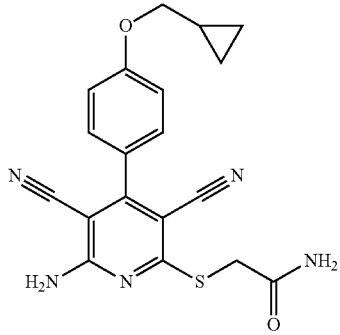 [SMILES: N#Cc1c(N)nc(SCC(N)=O)c(C#N)c1-c1ccc(OCC2CC2)cc1]

3-[4-[2-[[6-amino-9-[(2R,3R,4S,5S)-5-(ethylcarbamoyl)-3,4-dihydroxy-oxolan-2-yl]purin-2-yl]amino]ethyl] phenyl]propanoic acid, also known as CGS21680 and is an $A_{2A}$ receptor agonist.

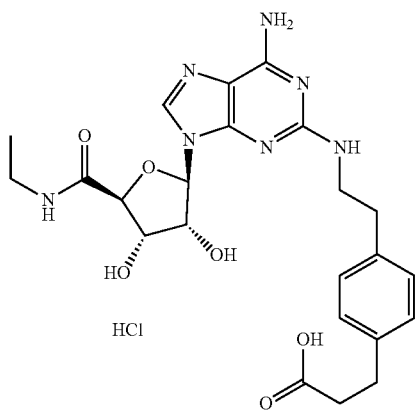 [SMILES: CCNC(=O)[C@H]1O[C@@H](n2cnc3c(N)nc(NCCc4ccc(CCC(=O)O)cc4)nc32)[C@H](O)[C@@H]1O ; Cl]

2-amino-8-[2-(4-morpholinyl)ethoxy]-4-phenyl-5H-indeno[1,2-d]pyrimidin-5-one, also known as JNJ40255293 and is an $A_{2A}/A_1$ receptor antagonist.

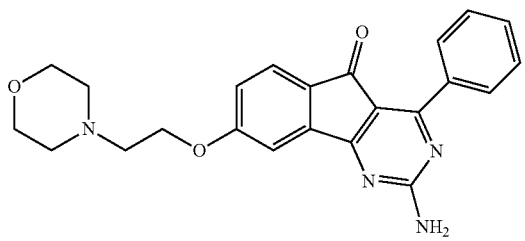 [SMILES: Nc1nc(-c2ccccc2)c2c(n1)-c1cc(OCCN3CCOCC3)ccc1C2=O]

8-[(E)-2-(3,4-dimethoxyphenyl)vinyl]-1,3-diethyl-7-methyl-3,7-dihydro-1H-purine-2,6-dione, also known as Istradefylline and is an $A_{2A}$ receptor antagonist.

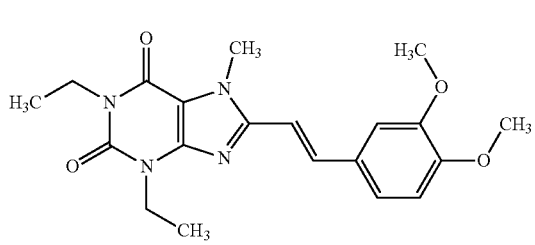 [SMILES: CCn1c(=O)c2c(nc(/C=C/c3ccc(OC)c(OC)c3)n2C)n(CC)c1=O]

4-(2-(7-amino-2-(furan-2-yl)-[1,2,4]triazolo[1,5-a][1,3,5] triazin-5-ylamino)ethyl)phenol, also known as ZM241385 and is an $A_{2A}$ receptor antagonist.

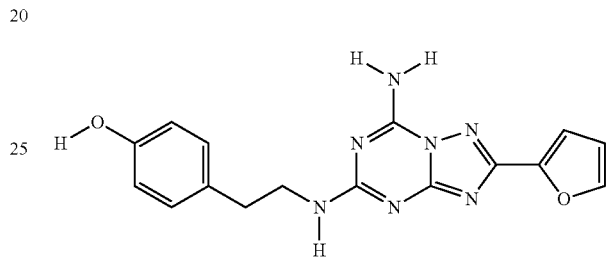

9-Chloro-2-(2-furanyl)-5-((phenylacetyl)amino)-[1,2,4] triazolo[1,5-c]quinazoline, also known as MRS-1220 and is an $A_3$ receptor antagonist.

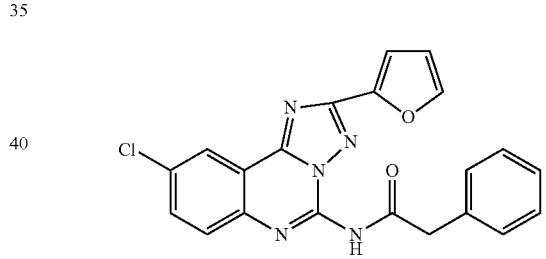

3-[(4-amino-3-methylphenyl)methyl]-7-furan-2-yltriazolo[5,4-d]pyrimidin-5-amine, also known as vipadenant and is an $A_{2A}$ receptor antagonist.

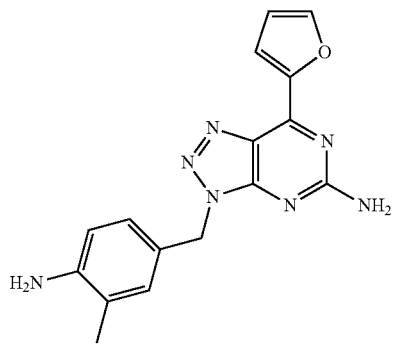 [SMILES: Cc1cc(Cn2nnc3c(-c4ccco4)nc(N)nc32)ccc1N]

2-(2-Furanyl)-7-[2-[4-[4-(2-methoxyethoxy)phenyl]-1-piperazinyl]ethyl]7H-pyrazolo[4,3-e][1,2,4]triazolo[1,5-c]pyrimidine-5-amine, also known as preladenant and is an $A_{2A}$ receptor antagonist.

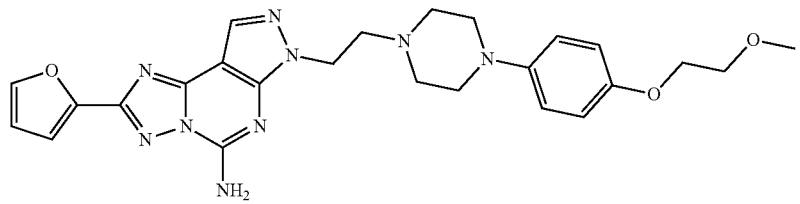 [SMILES: COCCOc1ccc(N2CCN(CCn3ncc4c3nc(N)n3nc(-c5ccco5)nc43)CC2)cc1]

4-hydroxy-N-(4-methoxy-7-morpholinobenzo[d]thiazol-2-yl)-4-methylpiperidine-1-carboxamide, also known as tozadenant and is an $A_{2A}$ receptor antagonist.

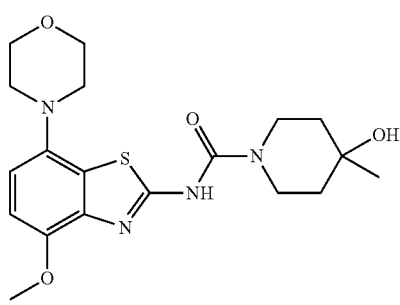 [SMILES: COc1ccc(N2CCOCC2)c2sc(NC(=O)N3CCC(C)(O)CC3)nc12]

2-butyl-9-methyl-8-(triazol-2-yl)purin-6-amine (ST-1535) is a $A_{2A}$ receptor antagonist.

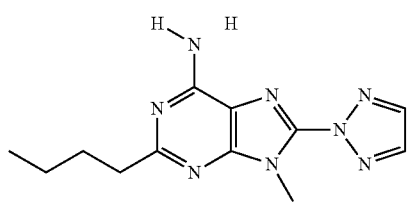

(6-Amino-9-methyl-8-(2H-1,2,3-triazol-2-yl)-9H-purin-2-yl)butan-2-one (ST4206) and is a $A_{2A}$ receptor antagonist.

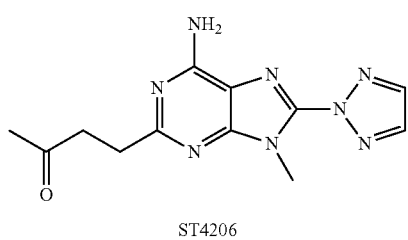 [SMILES: CC(=O)CCc1nc(N)c2nc(-n3nccn3)n(C)c2n1]

ST4206

Preferred are dual-targeting selective adenosine receptor modulators, such as ST-1535 and JNJ40255293. Optionally, the selective adenosine receptor modulator is JNJ40255293. These are selective $A_{2A}/A_1$ receptor antagonists.

In an aspect of the invention, the modulator or selective adenosine modulator is not caffeine, since caffeine works as a nonselective modulator of adenosine receptors ($A_1$, $A_{2a}$, $A_{2b}$ and $A_3$). Caffeine is not recommended by healthcare professionals where a subject is having difficulties in their rest-activity cycles. Indeed, if the timing of sleep for an individual is an issue, they are recommended to avoid stimulants such as caffeine altogether. Other nonselective antagonists or inverse agonists are similarly not recommended.

The scope of the invention embraces all pharmaceutically acceptable salt forms of adenosine receptor antagonists, inverse agonists and agonists, including any of the above-described specific compounds, which may be formed, e.g., by protonation of an atom carrying an electron lone pair which is susceptible to protonation, such as an amino group, with an inorganic or organic acid, or as a salt of a carboxylic acid group with a physiologically acceptable cation as they are well-known in the art. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, glycolate, nicotinate, benzoate, salicylate, ascorbate, or pamoate (embonate) salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; and acidic amino acid salts such as aspartate or glutamate salts.

Also included within the scope of pharmaceutically acceptable compositions are co-crystallised components. Co-crystals are multi-component crystals based on hydrogen bonding interactions without the transfer of hydrogen ions to form salts. Co-crystals have been described of various organic substances and given various names, such as addition compounds, molecular complexes, and heteromolecular co-crystals. Multi-component crystalline materials like co-crystals offer the prospect of optimised physical properties. Co-crystalline salts are also envisaged.

A peptide may include a compound containing two or more amino acids in which the carboxyl group of one acid is linked to the amino group of the other.

An siRNA is a nucleic acid that is a short, 15-50 base pairs and preferably 21-25 base pairs, double stranded ribonucleic acid. The term nucleic acid is a term of art that refers to a polymer containing at least two nucleotides. Natural nucleotides contain a deoxyribose (DNA) or ribose (RNA) group, a phosphate group, and a base. Bases include purines and pyrimidines, which further include the natural compounds adenine, thymine, guanine, cytosine, uracil, inosine, and natural analogues. Synthetic derivatives of purines and pyrimidines include, but are not limited to, modifications which place new reactive groups on the base such as, but not limited to, amines, alcohols, thiols, carboxylates, and alkylhalides. The term base encompasses any of the known base analogues of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. Nucleotides are the monomeric units of nucleic acid polymers and are linked together through the phosphate groups in natural polynucleotides. Natural polynucleotides have a ribose-phosphate backbone. Artificial or synthetic polynucleotides are polymerized in vitro and contain the same or similar bases but may contain a backbone of a type other than the natural ribose-phosphate backbone. These backbones include, but are not limited to: PNAs (peptide nucleic acids), phosphorothioates, phosphorodiamidates, morpholinos, and other variants of the phosphate backbone of natural polynucleotides.

The siRNA contains sequence that is identical or nearly identical to a portion of a gene. RNA may be polymerized in vitro, recombinant RNA, contain chimeric sequences, or derivatives of these groups. The siRNA may contain ribonucleotides, deoxyribonucleotides, synthetic nucleotides, or any suitable combination such that expression of the target gene is inhibited. The RNA is preferably double stranded, but may be single, triple, or quadruple stranded. An example of a single strand siRNA is an siRNA with a hairpin loop.

A protein refers herein to a linear series of greater than 2 amino acid residues connected one to another as in a polypeptide. A "therapeutic" effect of the protein in attenuating or preventing the disease state can be accomplished by the protein either staying within the cell, remaining attached to the cell in the membrane, or being secreted and dissociated from the cell where it can enter the general circulation and blood.

The term "antibody" encompasses polyclonal or monoclonal antibodies, natural, synthetic or recombinant antibodies, camelid single-domain antibodies, chimeric antibodies such as a humanized antibodies, and the fragments thereof (e.g. Fab'2, Fab, Fv, scFv) having retained their ability to act as agonist or antagonist of an adenosine receptor.

The modulators, selective modulators or compositions of the invention may also be provided as pro-drugs or any other bioprecursor which are converted in use into the active agents.

It will be appreciated that the term "treatment" and "treating" as used herein means the management and care of a subject for the purpose of combating a condition, such as a disease or a disorder. The term is intended to include the full spectrum of treatments for a given condition from which the subject is suffering, such as administration of the adenosine receptor modulator to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a subject for the purpose of combating the disease, condition, or disorder and includes the administration of the adenosine receptor modulators to prevent the onset of the symptoms or complications. The subject to be treated is preferably a mammal, in particular a human, but it may also include animals, such as dogs, cats, horses, cows, sheep and pigs.

According to a further aspect the invention provides the use of an adenosine receptor modulator, selective modulator or composition according to the invention in the manufacture of a medicament for the treatment of circadian rhythm disorders.

The circadian rhythm disorder may be a circadian rhythm dysfunction or a circadian rhythm sleep disorder. As used herein, circadian rhythm dysfunctions do not include circadian rhythm sleep disorders.

According to a further aspect, the invention provides a use of the adenosine receptor modulator, selective modulator or composition according to the invention in the treatment of circadian misalignment.

According to a yet further aspect, the invention provides a use of the adenosine receptor modulator, selective modulator or composition according to the invention for modifying a biological clock. The modulation may be to delay or advance the biological clock with respect to the external or environmental clock depending on the timing of the drug administration.

The invention also provides a pharmaceutical composition comprising an adenosine receptor modulator, selective modulator or composition according to the invention and a pharmaceutical acceptable carrier.

Pharmaceutical compositions to be used comprise a therapeutically effective amount of an adenosine receptor modulator, selective modulator or composition or a pharmaceutically acceptable salt or other form thereof, together with one or more pharmaceutically acceptable excipients, such as carriers, diluents, fillers, disintegrants, lubricating agents, binders, colorants, pigments, stabilizers, preservatives, antioxidants, and/or solubility enhancers.

The pharmaceutical compositions can be formulated by techniques known in the art, such as the techniques published in Remington's Pharmaceutical Sciences, 20th Edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. The pharmaceutical composition may be formulated as a dosage form for oral administration.

Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The adenosine receptor modulator, selective modulator, composition or the above-described pharmaceutical compositions comprising one or more adenosine receptor agonists/inverse agonists/antagonists may be administered to the subject by any convenient route of administration, whether systemically/peripherally or at the site of desired action, including but not limited to one or more of oral (e.g., as a tablet, capsule, or as an ingestible solution), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, and vaginal.

If the modulators, selective modulators, compositions or the pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known in the art.

The modulators or pharmaceutical compositions can also be administered orally in the form of tablets, capsules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Alternatively, the modulators, selective modulators, compositions or pharmaceutical compositions can be administered in the form of a suppository or pessary, or may be applied topically in the form of a gel, hydrogel, lotion, solution, cream, ointment or dusting powder. They may also be dermally or transdermally administered, for example, by the use of a skin patch.

The modulators, selective modulators, compositions or pharmaceutical compositions may also be administered by sustained release systems. Suitable examples of sustained-release compositions include semi-permeable polymer matrices in the form of shaped articles, e.g., films, or microcapsules. Sustained-release matrices include, e.g., polylactides (U.S. Pat. No. 3,773,919), copolymers of L-glutamic acid and gamma-ethyl-L-glutamate (Sidman, U. et al., 1983), poly(2-hydroxyethyl methacrylate) (Langer, R. et al., 1981; Langer, R. et al., 1982), ethylene vinyl acetate (Langer, R. et al., 1981; Langer, R. et al., 1982) or poly-D-(−)-3-hydroxybutyric acid (EP133988). Sustained-release pharmaceutical compositions also include liposomally entrapped compounds. Liposomes containing an EGFR inhibitor/antagonist can be prepared by methods known in the art, such as, e.g., the methods described in any one of: DE3218121; Epstein et al., 1985; Hwang et al., 1980; EP0052322; EP0036676; EP088046; EP0143949; EP0142641; JP 83-118008; U.S. Pat. Nos. 4,485,045 and 4,544,545; and EP0102324.

The modulators, selective modulators, compositions or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the modulators, selective modulators, compositions or pharmaceutical compositions for pulmonary administration, particularly inhalation. Such dry powders may be prepared by spray drying under conditions which result in a substantially amorphous glassy or a substantially crystalline bioactive powder. Accordingly, dry powders of the EGFR inhibitors/antagonists can be made according to the emulsification/spray drying process disclosed in WO 99/16419 or WO01/85136. Spray drying of solution formulations of the compounds of the present invention is carried out, for example, as described generally in the "Spray Drying Handbook", 5th ed., K. Masters, John Wiley & Sons, Inc., NY, NY (1991), and in WO 97/41833 or WO 03/053411.

For topical application to the skin, the modulators, selective modulators, compositions or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

The pharmaceutical composition may contain an excipient to facilitate transport across the blood brain barrier. As used herein, the 'blood-brain barrier' or 'BBB' refers to the barrier between the peripheral circulation and the brain and the spinal cord which is formed by tight junctions within the brain capillary endothelial plasma membranes, creating an extremely tight barrier that restricts the transport of molecules into the brain. The excipient which facilitates transport across the blood brain barrier refers to a substance that is capable of disrupting or penetrating the blood brain barrier. The amount of excipient administered with the adenosine receptor modulator is the amount effective to disrupt the blood brain barrier and allow the adenosine receptor modulator to enter the brain.

In a preferred embodiment, the modulators, selective modulators, compositions or pharmaceutical compositions may be administered by the oral route.

The modulators, selective modulators, compositions or pharmaceutical compositions may also be administered by the intranasal route. Advantages of the intranasal route include:
- unlike parenteral administration, the intranasal administration is not invasive, is generally well tolerated and is easy to self-manage;
- unlike what happens after oral administration, the substance administered does not have to pass through the digestive system of the gastrointestinal tract or undergo hepatic metabolization;
- the available area of nasal mucosa for absorption is relatively large and easily accessible;
- and given that dwell time of the substance in the nose is short, the haematic concentration peak is quickly reached and this can be time by time controlled.

In a further aspect, the invention provides a method for treating or preventing circadian rhythm disorders, the method comprising administering to a subject in need thereof a therapeutically effective amount of an adenosine receptor modulator, selective modulators, composition or a pharmaceutical composition of the invention.

An effective amount is dose is the amount that over a period of time of treatment, which may be, e.g. 1 day or multiple weeks, results in entrainment of the patient to a 24 hour circadian rhythm. The effective amount may be required as multiple doses over 24 hours or as one administration.

The daily dose of an adenosine receptor modulator, selective modulator or composition of the invention will, in general, be in the range of about 0.1 mg to about 1000 mg, e.g. about 1 mg to about 100 mg, about 10 mg to about 100 mg or about 20 mg to about 50 mg.

For the prevention or treatment of jet-lag in subjects travelling eastwards, the adenosine receptor antagonist may be taken during the day, preferably between about 7 am and about 2 μm.

The adenosine receptor agonist may be taken very early in the morning, preferably between about 4 am to about 7 am for the prevention or treatment of jet-lag disorder in subjects travelling eastwards.

It is preferred that the time of administration is dictated by the Circadian Time (CT) of the rhythm to be modified. The CT can be determined as mentioned previously by various assays and observations. For advancing the biological clock or circadian rhythm, it is preferred that administration is at selective modulator or composition between about CT4 to 8, preferably between CT5 and 7, or at CT6. To "advance" the circadian rhythm means to bring the rhythm forwards in the external day.

In order to delay the circadian rhythm of an individual (or a cell, tissue or organ thereof) according to any aspect or embodiment of the invention, it is preferred to administer the modulator, selective modulator or composition between about CT14 to 18, preferably between CT15 and 17, or at CT16. To "delay" the circadian rhythm means to push the rhythm backwards in the external day.

The present invention particularly may relate to a composition comprising at least one selective adenosine receptor modulator, wherein said composition antagonises the $A_1$ and $A_{2A}$ adenosine receptors, for use in the treatment of circadian rhythm disorders or circadian rhythm dysfunctions, for modulating a biological clock or for treating circadian misalignment. In this aspect of the invention, the selective modulator or modulators have a limited or no affinity for the $A_{2B}$ and/or $A_3$ adenosine receptors.

The present invention can be carried out in conjunction with other treatment approaches, e.g. in combination with a second or multiple other active pharmaceutical agents, including but not limited to other agents that affect insomnia, sleep-wake patterns, vigilance, depression, or psychotic episodes.

It may be desirable to combine treatment with the modulator, selective modulator or compositions of the invention with other pharmacological or therapeutic interventions. These interventions may be most effective, or have the least side effects, at a particular CT or window of CT. Examples of such inventions include anticancer therapy, cardiovascular, respiratory, anti-inflammatory, immunosuppressive, antiepileptic, antipyretic, analgesic, antimalarial, antibiotic, antiseptic, mood stabilizing, hormone replacing, contraceptive or any other therapy.

It will be appreciated that optional features applicable to one aspect or embodiment of the invention can be used in any combination, and in any number. Moreover, they can also be used with any of the other aspects or embodiments of the invention in any combination and in any number. This includes, but is not limited to, the dependent claims from any claim being used as dependent claims for any other claim in the claims of this application.

The invention will be further described, by means of non-limiting example only, with reference to the following figures and experimental examples.

FIGS. 1A-1I—demonstrate that adenosine receptor agonists activate clock gene expression in U2OS cells.

FIG. 1A—shows Per2::Luc U2OS cells treated with IB-MECA with the time of application indicated by the arrow.

Figure 1B:
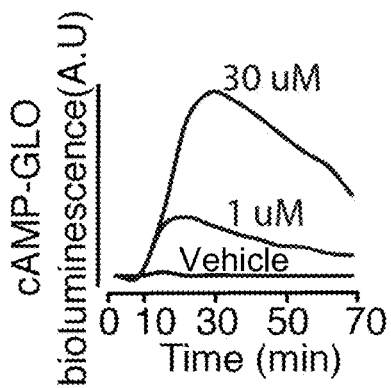

FIG. 1B—demonstrates that IB-MECA increases intracellular second messenger cAMP in a dose responsive manner.

Figure 1C:
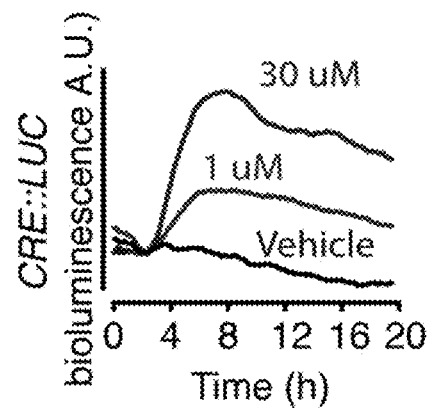

FIG. 1C—demonstrates that IB-MECA increases transcription driven by the CREB, as indicated by the CRE::Luc reporter.

Figure 1D:
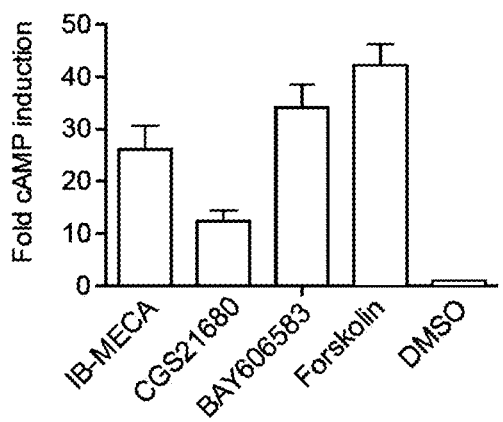

FIG. 1D—demonstrates cAMP induction by adenosine receptor agonists.

Figure 1E:
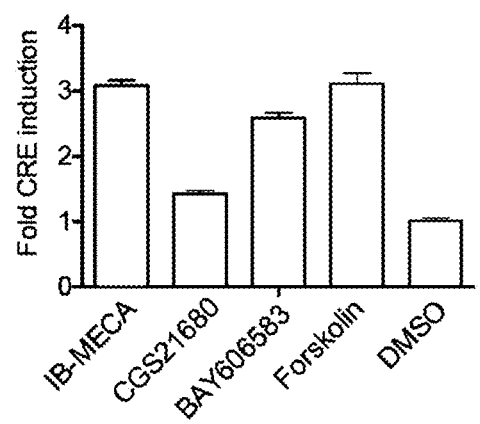

FIG. 1E—demonstrates CREB induction by several adenosine receptor agonists, Forskolin was included as a positive control.

Figure 1F:
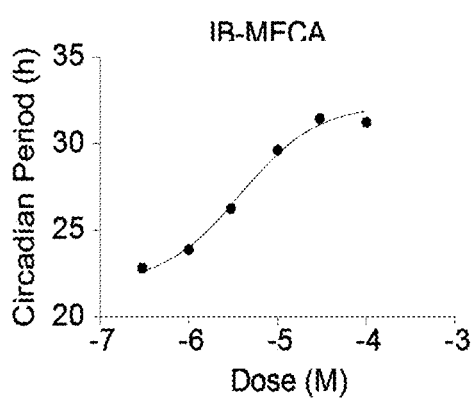

FIG. 1F—demonstrates dose responsive period lengthening in IB-MECA treated U2OS cells.

Figure 1G:
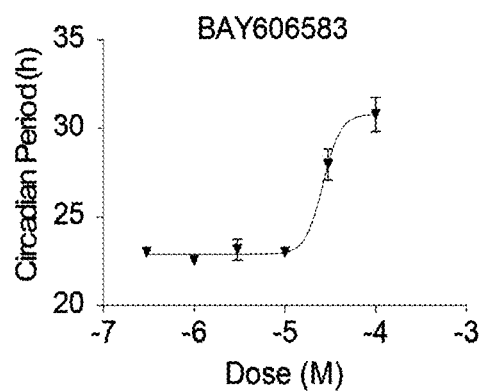

FIG. 1G—demonstrates dose responsive period lengthening in BAY606583 treated U2OS cells.

Figure 1H:
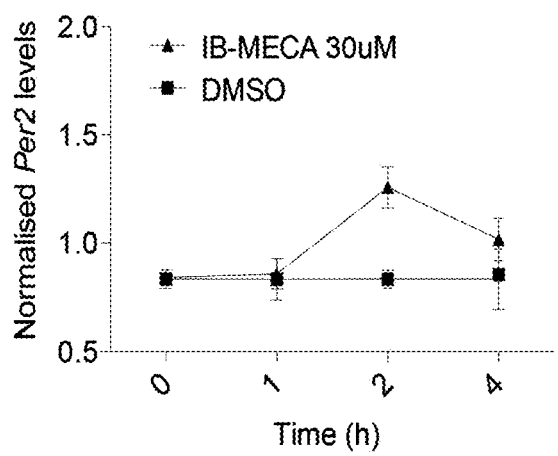

FIG. 1H—demonstrates that Per1 mRNA levels are elevated after IB-MECA application in U2OS cells as measured by qPCR.

Figure 1I:
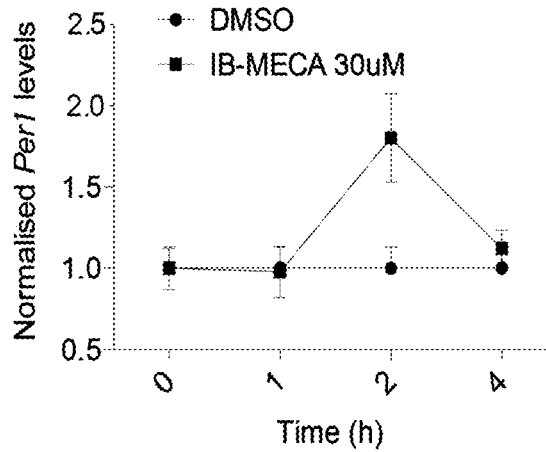

FIG. 1I—demonstrates that Per2 mRNA levels are elevated after IB-MECA application in U2OS cells as measured by qPCR.

Figure 1J:
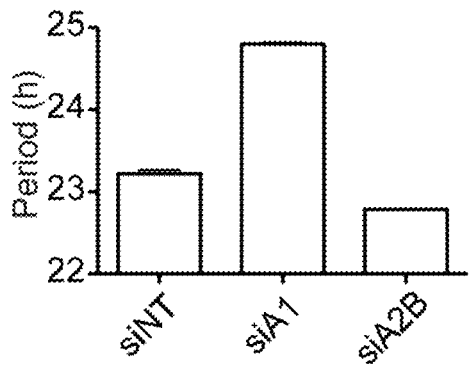

FIG. 1J—demonstrates that siRNA-mediated knockdown of individual adenosine receptors (Adora1—siA1, blue, Adora2b—siA2B) alters circadian period in opposite directions.

Figure 1K:
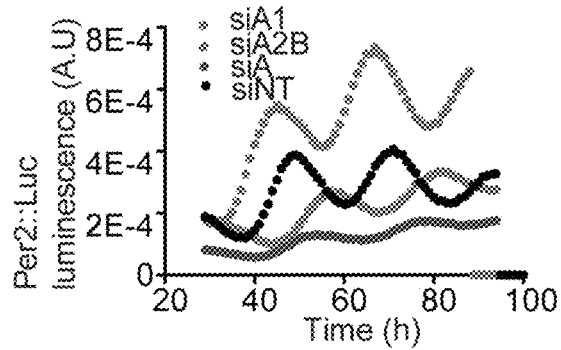
Figure 1L:
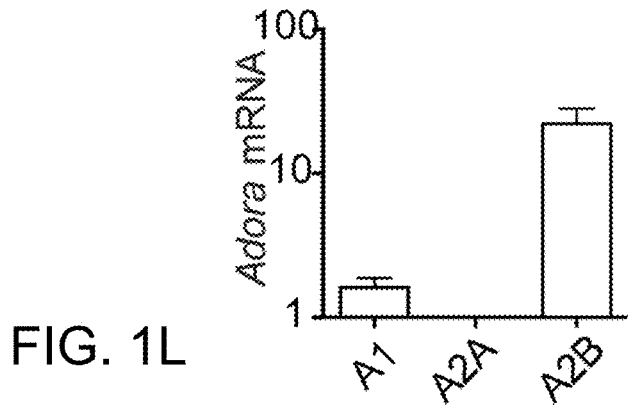

FIG. 1K—Individual traces from siRNA knockdown shown here, knockdown of all adenosine receptors (siA) severely dampening rhythms. Also shown are the knockdown of the different receptor subtypes individually and the effect on rhythms.

FIG. 1—demonstrates reception expression levels of Adora1, 2a and 2b in U2OS cells.

Figure 1M:
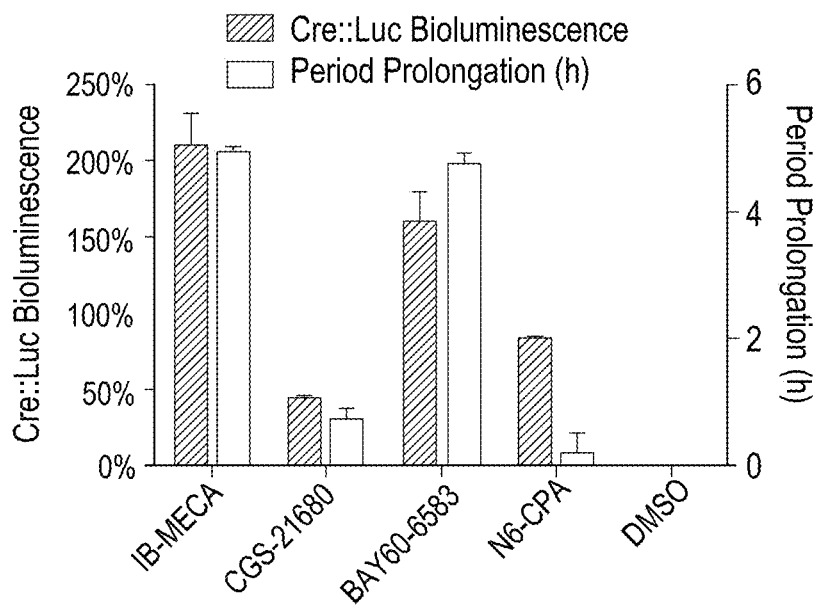

FIG. 1M—demonstrates that period elongation in Per2::Luc U2OS cells shows a tight correlation with the levels of CRE::Luc induction.

Figure 2A:
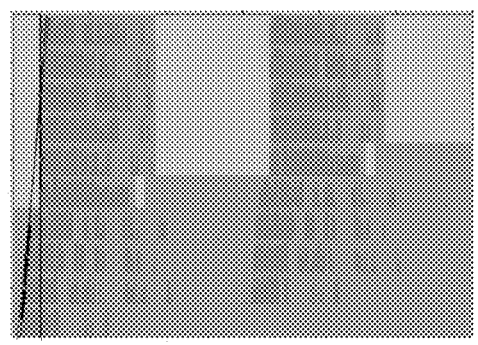
FIGS. 2A-2B are normal phase shifting and attenuated phase shifting, respectively, of circadian activity in response to a light pulse in the early part of the morning phase shifting data.
Figure 2B:
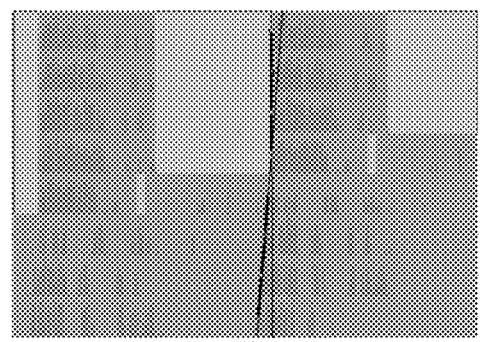
Figure 2C:
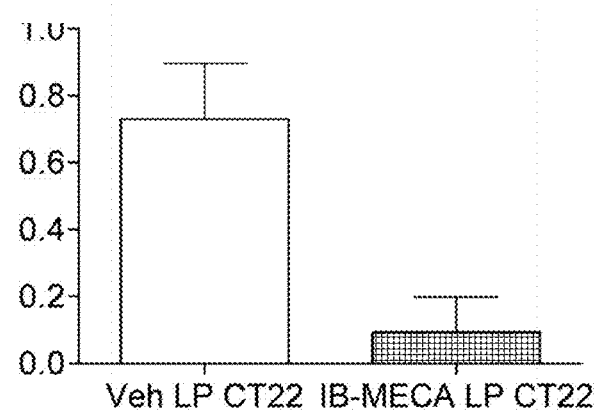
FIG. 2C is a graph which demonstrates a summary of the phase shifting data, n=6, IB-MECA attenuates the phase-shifting effect of light administered at time CT22.

FIGS. 2A-2C—demonstrate in vivo the ability of adenosine receptor agonists to phase shift circadian rhythms and modulate the effect of light on the central circadian clock.

FIG. 2A—demonstrates normal phase shifting of circadian activity in response to a light pulse in the early part of the morning. Animals were maintained in a 12 h light (white) 12 h dark (grey) cycle and vehicle was administered just before a 30 min 400 lux light pulse (white bar) at time CT 22 (or 10 hours after lights off). All light cues were then removed to allow the animals free running clock to express. A gap in the lines on the day after the light pulse was administered indicates a phase shift.

FIG. 2B—demonstrates attenuated phase shifting of circadian activity in response to a light pulse in the early part of the morning. Animals were maintained in a 12 h light (white) 12 h dark (grey) cycle and IB-MECA (1 mg/kg) was administered just before a 30 min 400 lux light pulse (white bar) at time CT 22 (or 10 hours after lights off).

FIG. 2C—demonstrates a summary of the phase shifting data, n=6, IB-MECA attenuates the phase-shifting effect of light administered at time CT22.

FIGS. 3A-3K—demonstrate that adenosine receptor antagonists modulate circadian rhythms and clock gene expression in U2OS cells.

Figure 3A:
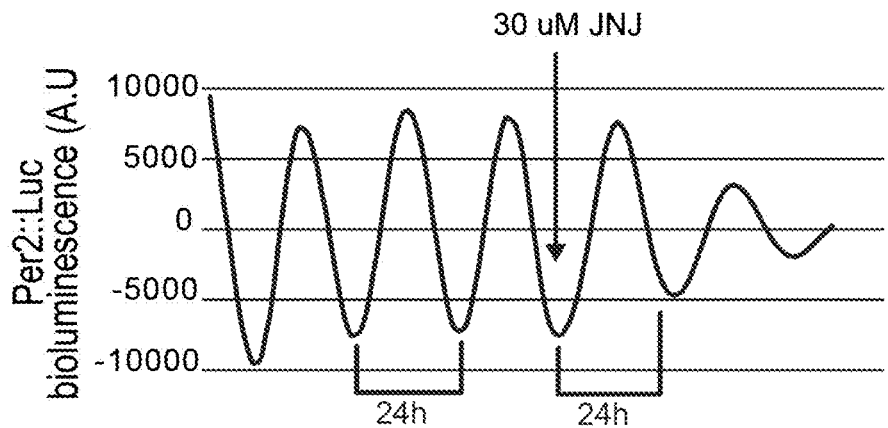
FIGS. 3A-3K are graphs which demonstrates that adenosine receptor antagonists modulate circadian rhythms and clock gene expression in U2OS cells.

FIG. 3A—demonstrates Per2::Luc U2OS cells treated with JNJ40255293 with the time of application indicated by the arrow. Period lengthening was observed.

Figure 3B:
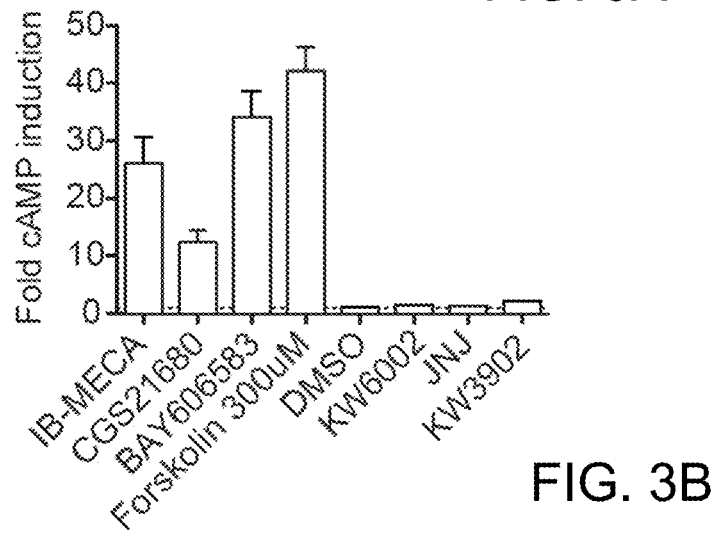

FIG. 3B—demonstrates that none of the adenosine receptor antagonists tested induce expression from CRE-elements, as indicated by a CRE::Luc reporter (Forskolin used as positive control). Drugs tested at 30 uM.

Figure 3C:
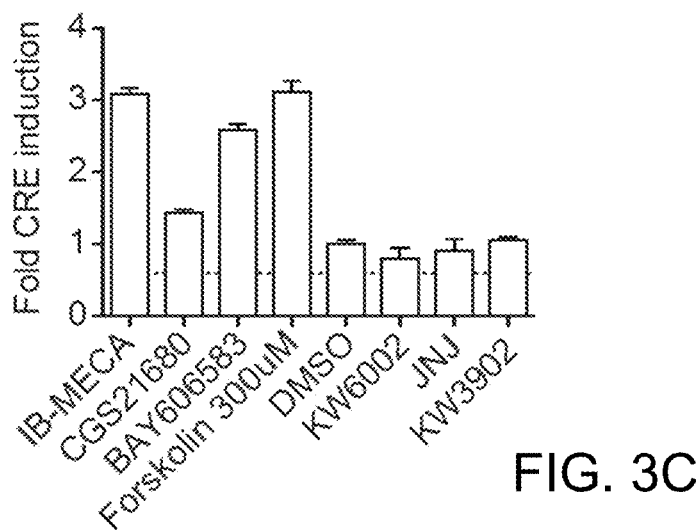

FIG. 3C—demonstrates that none of the adenosine receptor antagonists tested induce cAMP production, as indicated by a cAMP-GLO reporter (Forskolin used as positive control). Drugs tested at 30 uM.

Figure 3D:
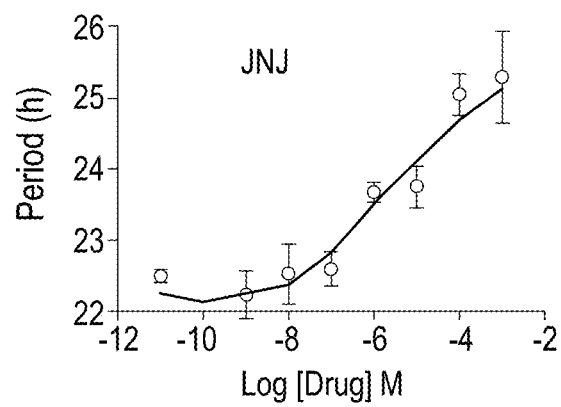

FIG. 3D—demonstrates dose responsive period lengthening in JNJ40255293 treated U2OS cells.

Figure 3E:
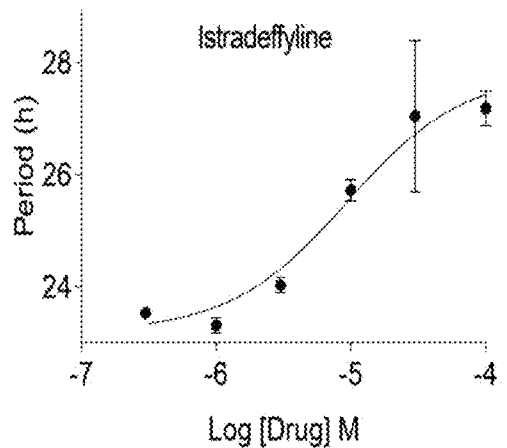

FIG. 3E—demonstrates dose responsive period lengthening in Istradefylline treated U2OS cells.

Figure 3F:
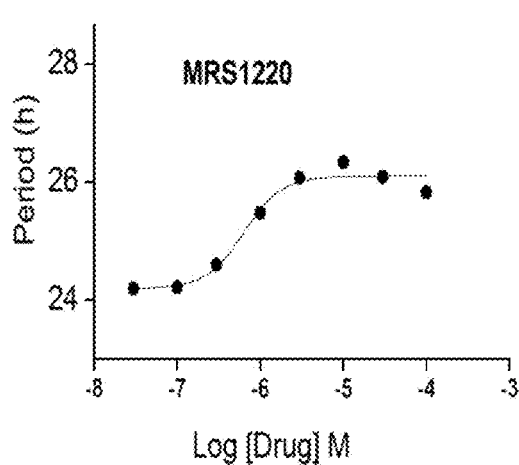

FIG. 3F—demonstrates dose responsive period lengthening in MRS1220 treated U2OS cells.

Figure 3G:
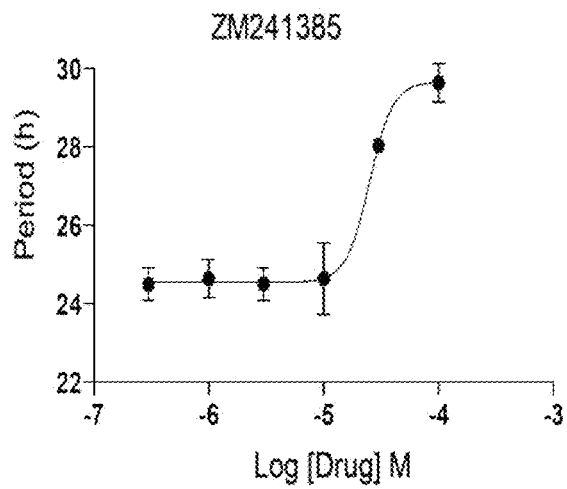

FIG. 3G—demonstrates dose responsive period lengthening in ZM241385 treated U2OS cells.

Figure 3H:
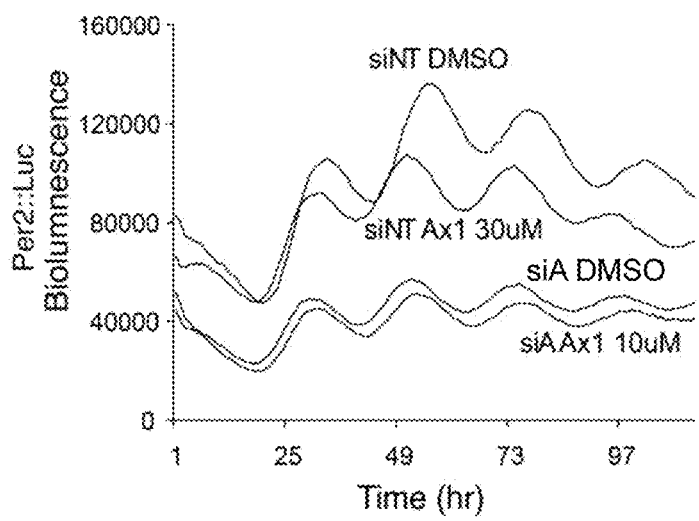

FIG. 3H—To test that the period lengthening effect of adenosine receptor antagonism was due to action on adenosine receptors, all adenosine receptors expressed in U2OS cells were knocked down and it was found that the effect of CGS15943 (Ax1) was lost.

Figure 3I:
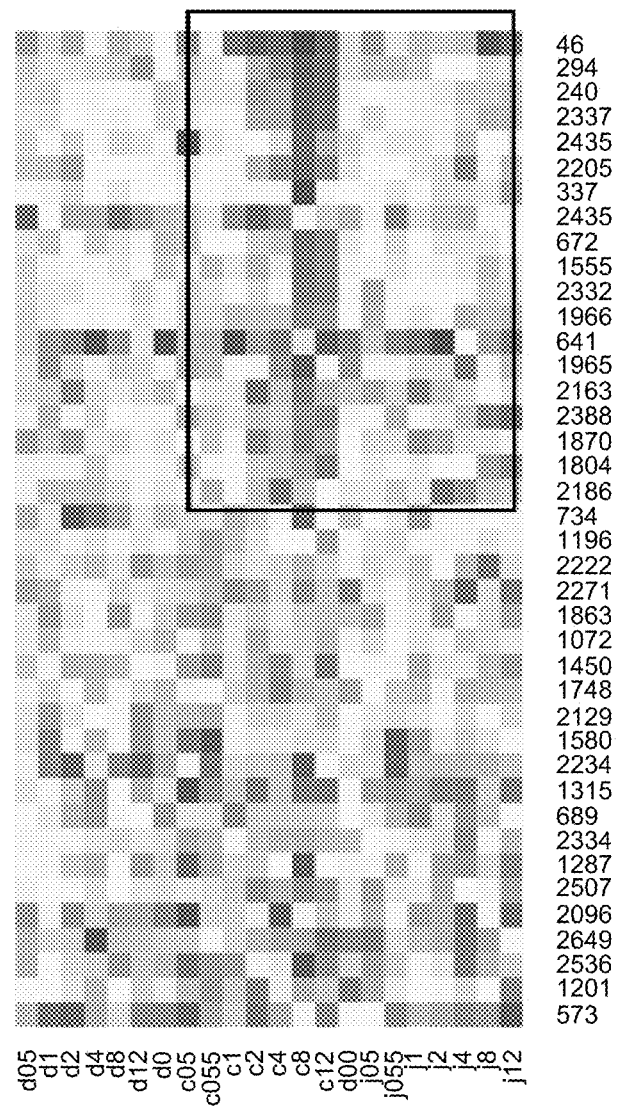

FIG. 3I—To understand the transcription factor responsible for the observed changes in rhythm, STAR-PROM screening was conducted and nucleic acid signatures switched on by JNJ40255293 (inside the box) were identified.

Figure 3J:
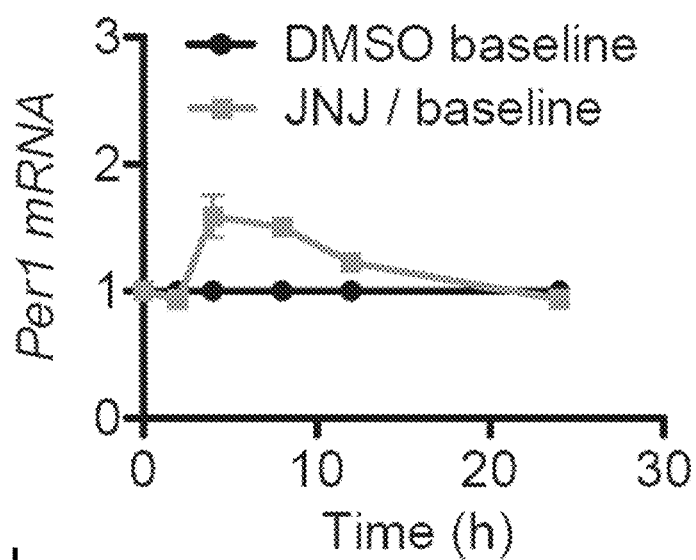

FIG. 3J—demonstrates that Per1 mRNA levels are elevated after JNJ40255293 application in U2OS cells as measured by qPCR.

Figure 3K:
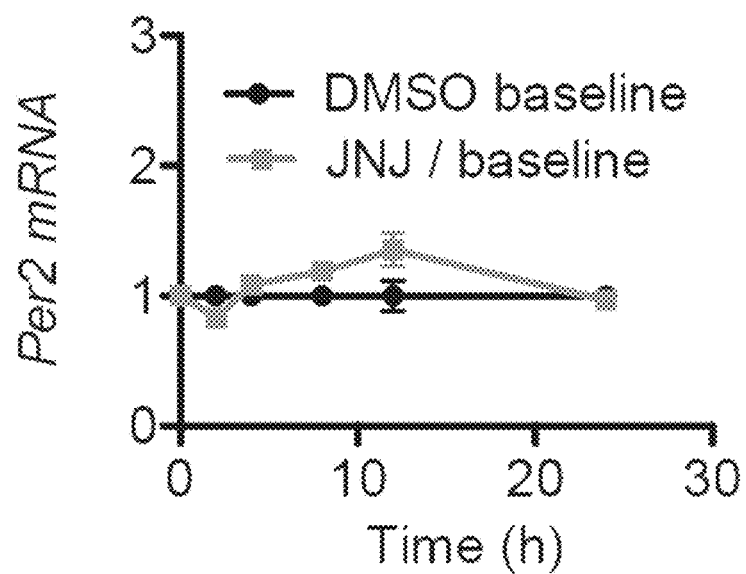

FIG. 3K—demonstrates Per2 mRNA levels are elevated after JNJ40255293 application in U2OS cells as measured by qPCR.

FIGS. 4A-4K—demonstrate that in vivo adenosine receptor antagonists phase shift circadian rhythms and enhance re-entrainment in a jet-lag protocol.

FIG. 4A—demonstrates a control animal released from entrained conditions to free-run. Actograms from C57B/6 male mice (80+ days) housed in a 12 h-light 12 h-dark cycle (400 lux). Stable entrainment as indicated by onset of activity (black) during the dark part of the cycle (grey). Animals were administered Vehicle (A) or JNJ40255293, 5 mg/kg intraperitoneal injection (B) (arrow, 6 h after the onset of light).

FIG. 4B—demonstrates a JNJ40255293 treated animal (star) in an identical set up as FIG. 4A. JNJ40255293 induced a phase advance, indicated by the advance in activity (diagonal line) after the animals are housed in constant dark (grey).

FIG. 4C—demonstrates the phase shift induced by administration of the indicated drug (IB-MECA 1 mg/kg, JNJ40255293 5 mg/kg and CGS15943 5 mg/kg) at time ZT6.

FIG. 4D—demonstrates the phase shift induced by administration of the indicated drug (IB-MECA 1 mg/kg, JNJ40255293 5 mg/kg and CGS15943 5 mg/kg) at time CT16.

FIG. 4E—demonstrates re-entrainment in a jet-lag protocol in a control vehicle-treated animal. The same protocol as FIGS. 4A and 4B was adopted, except rather than release the animals into constant dark after drug administrations, the light-dark cycle was advanced 6 h to simulate an eastward flight and an advance of 6 time zones. The vehicle treated animals (E) advanced their activity gradually each day.

FIG. 4F—demonstrates re-entrainment in a jet-lag protocol in a JNJ40255293 (5 mg/kg) treated animal. The same protocol as FIG. 4E was adopted. The drug-treated animals advanced their activity much more rapidly than the controls.

Figure 4G:
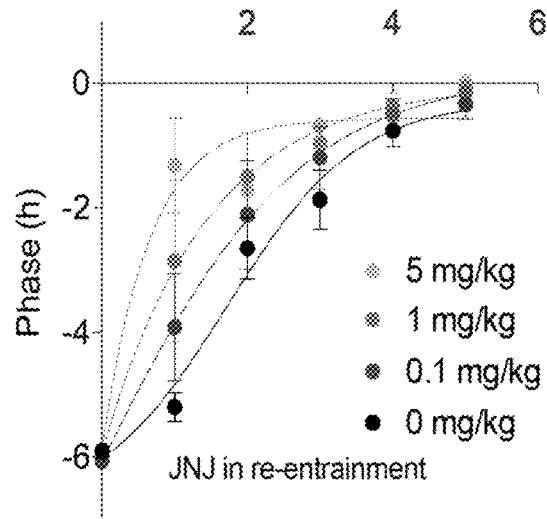
FIGS. 4G-4K are graphs.

FIG. 4G—demonstrates the dose response curve for re-entrainment in a jet-lag protocol, JNJ40255293 dose responsively enhanced re-entrainment.

Figures 4H, 4I:
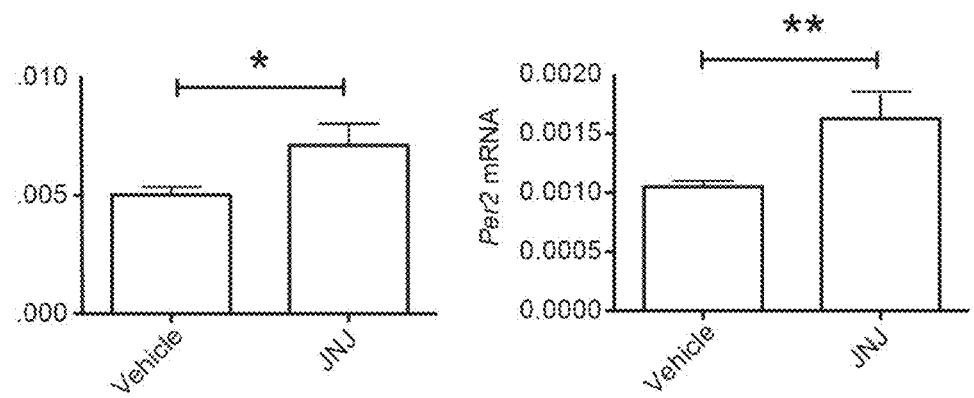

FIG. 4H—demonstrates that Per1 mRNA levels are elevated within the SCN after JNJ40255293 administration in the periphery (intra-peritonially).

FIG. 4I—demonstrates that Per2 mRNA levels are elevated within the SCN after JNJ40255293 administration in the periphery (intra-peritonially).

Figure 4J:
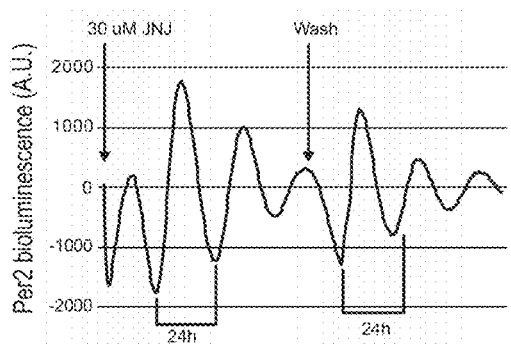

FIG. 4J—shows the Per2::Luc rhythms from SCN explants from Per2::Luc transgenic animals. JNJ40255293 (10 uM) added at the arrow.

Figure 4K:
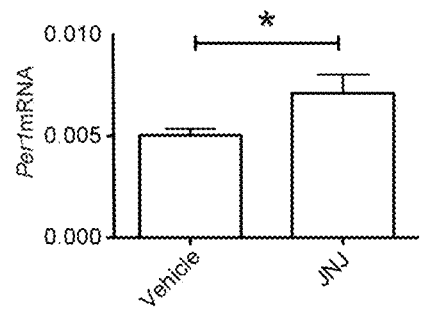

FIG. 4K—demonstrates the administration of 5 mg/kg JNJ40255293 and onsets of activity measured.

FIGS. 5A to 5F show that adenosine receptor antagonists/inverse agonists regulate cellular clocks via a CREB-independent signalling pathway, implicating another signalling system. Experimental work here is conducted with JNJ40255293.

Figure 5A:
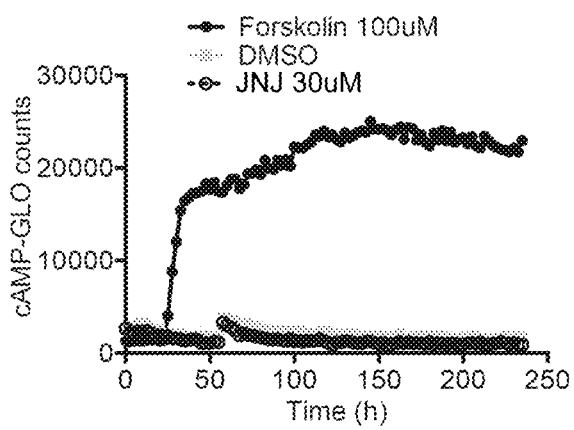
FIGS. 5A-5E are graphs detailing the effect of adenosine receptor antagonist on a cellular clock.

FIG. 5A—demonstrates that JNJ40255293 does not elevate cAMP levels in U2OS cells.

Figure 5B:
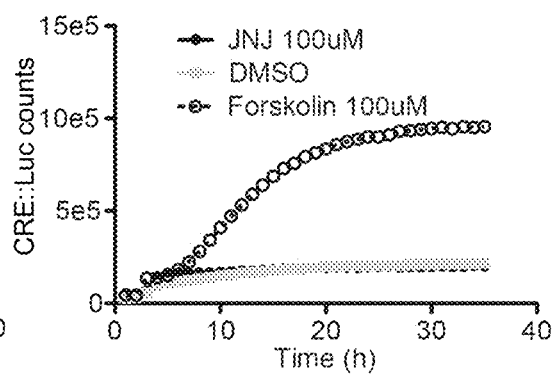

FIG. 5B—shows that JNJ40255293 does not increase signals from the CRE::Luc reporter in contrast to the positive control Forskolin.

Figure 5C:
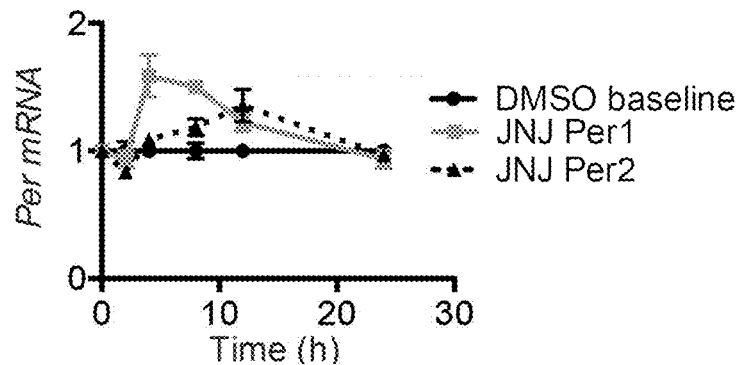

FIG. 5C—demonstrates robust increases in Per1 and Per2 mRNA are seen after treatment with 10 uM JNJ40255293 when applied to U2OS cell cultures.

Figure 5D:
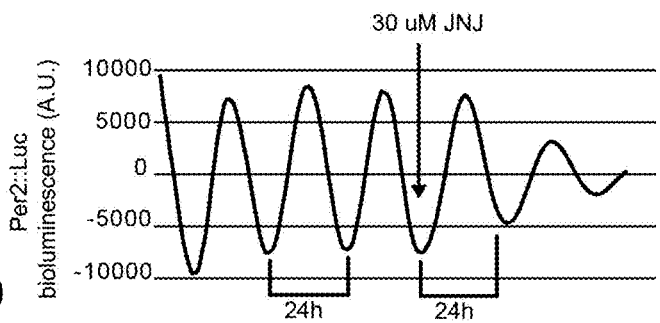

FIG. 5D—shows that treatment with 10 uM JNJ40255293 leads to increases in period length in Bmal1::Luc reporter U2OS cells which revert to normal rhythms after washout of drug.

Figure 5E:
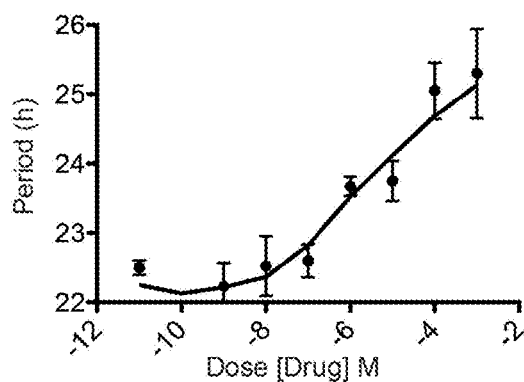

FIG. 5E—demonstrates that a dose-responsive increases in period length are observed.

FIGS. 6A to 6F—depict data that shows that adenosine receptor antagonists that target two or more receptors elevate expression of both Per1 and Per2, antagonists that act on only single receptors do not have this effect.

Figure 6A:
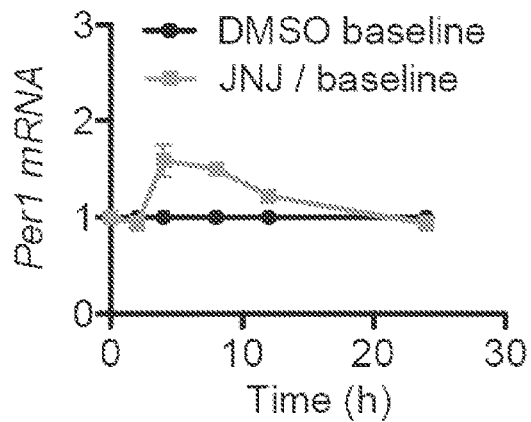
FIGS. 6A-6D are graphs depicting data that shows that adenosine receptor antagonists that target two or more receptors elevate expression of both Per1 and Per2, antagonists that act on only single receptors do not have this effect.
Figure 6B:
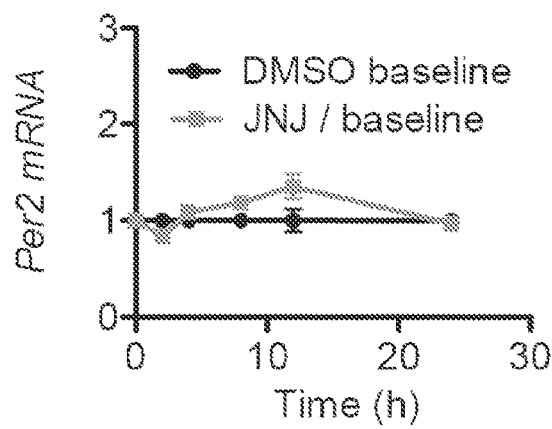
Figure 6C:
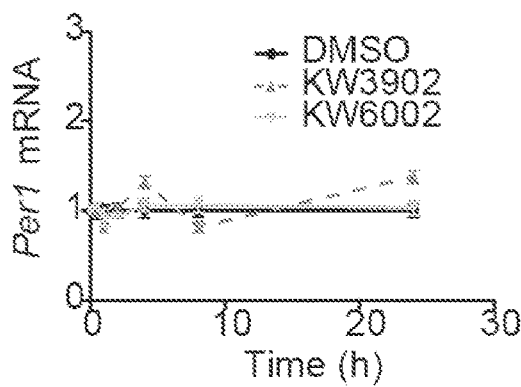
Figure 6D:
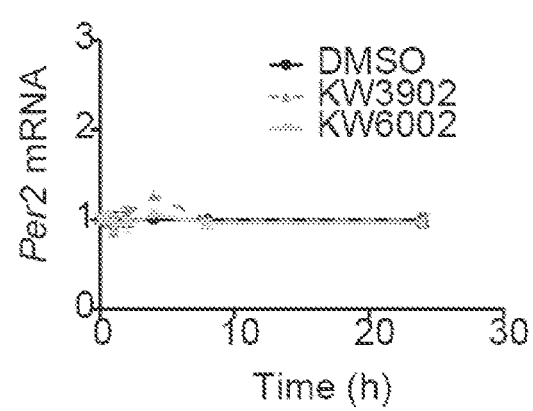
Figure 6E:
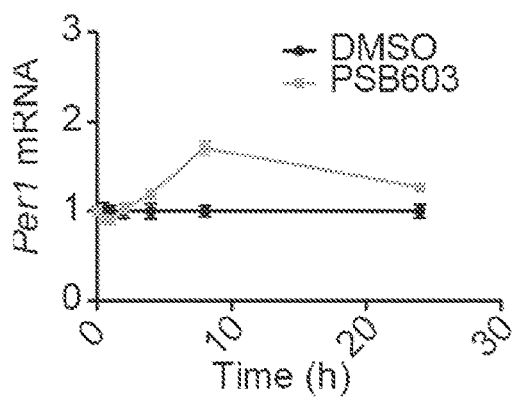
Figure 6F:
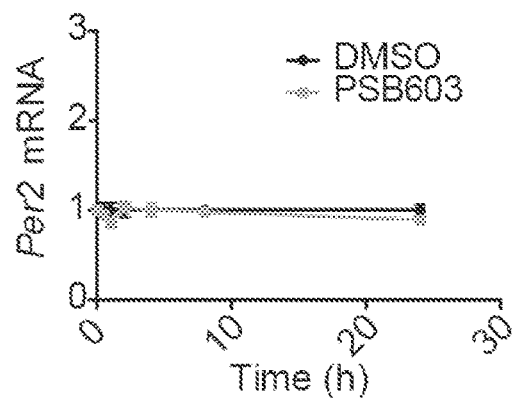

FIG. 6D—shows the effect of JNJ40255293 is mediated by adenosine receptors with dose-responsive period lengthening in Per2::Luc U2OS cells;

FIGS. 6A to 6F—demonstrate the levels of Per1 and Per2 detected after treatment with (6A and 6B) JNJ4055213 (6C and 6D) KW3902 and KW6002 and (6E and 6F) PSB603. Mixed $A_{2A}/A_1$ antagonists such as JNJ 4055213 induce the expression of Per1 and Per2 in U2OS cells, but not specific $A_1$(KW3902), $A_{2A}$(KW6002) or $A_{2B}$(PSB) antagonists.

FIGS. 7A to 7C—show that the STAR-PROM approach reveals a novel signalling pathway downstream of adenosine receptor inhibition that converges on the circadian clock.

FIGS. 7A and 7B—demonstrate Upregulation of Fos mRNA (7A) and cJun (7B) after treatment with 10 uM JNJ40255293.

FIG. 7C—shows the activity of Seq3 after knockdown of AP1 (composed of FOS and JUN) when compared with a non-targeting siRNA (siNT) and induction by JNJ40255293 (10 uM) compared with DMSO.

Figure 8A:
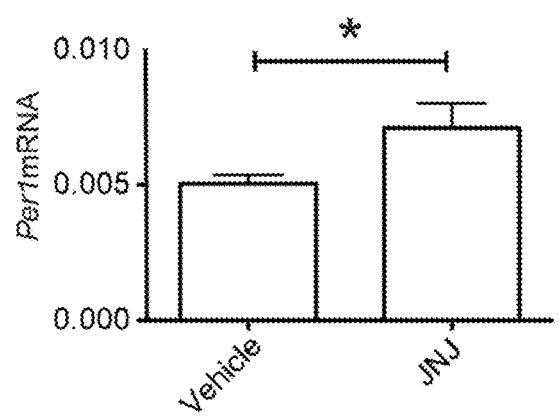
FIGS. 8A-8B are graphs that show Per1(A) and Per2 (B) mRNA levels increase within the SCN 4 h after intraperitoneal injection of JNJ40255293.
Figure 8B:
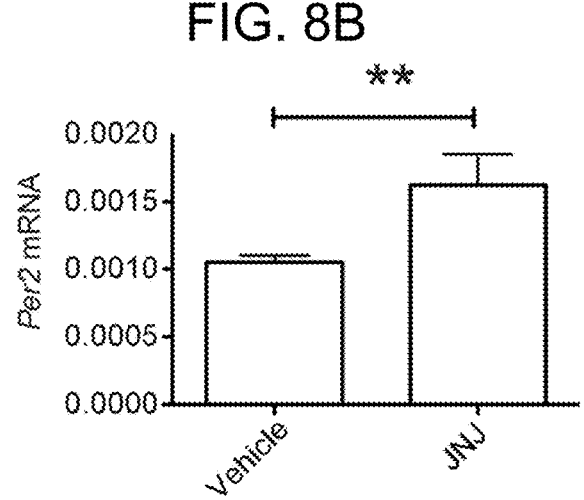
Figure 8C:
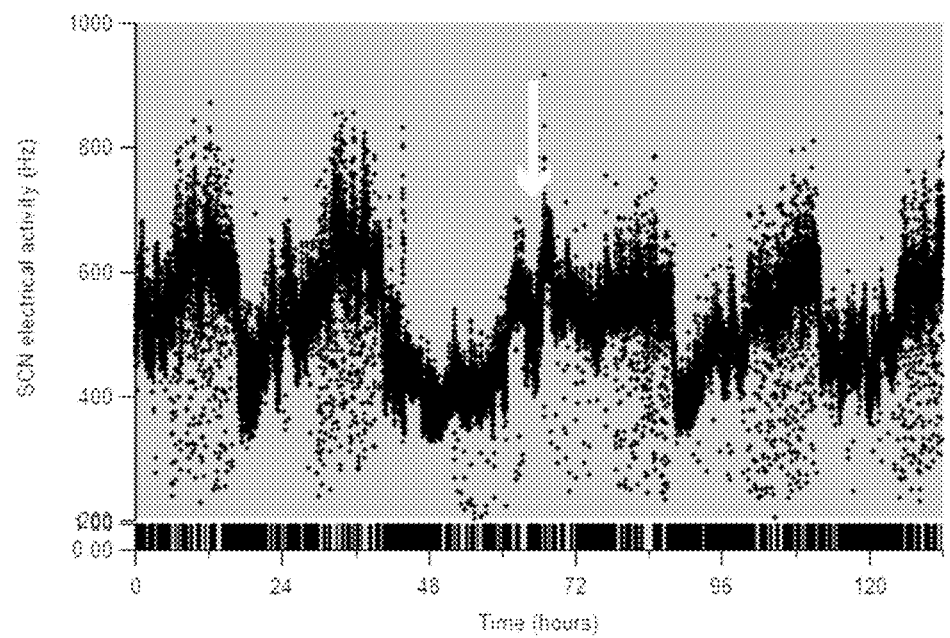
FIG. 8C is an in vivo recording from SCN electrode implanted animals show a marked phase shift of SCN electrical activity on intraperitoneal injection of JNJ40255293 (5 mg/kg).

FIGS. 8A-8C—show that the SCN sensitive to adenosine receptor antagonists.

FIGS. 8A and 8B—show Per1(A) and Per2 (B) mRNA levels increase within the SCN 4 h after intraperitoneal injection of JNJ40255293.

FIG. 8C—is an in vivo recording from SCN electrode implanted animals show a marked phase shift of SCN electrical activity on intraperitoneal injection of JNJ40255293(5 mg/kg).

Figure 9A:
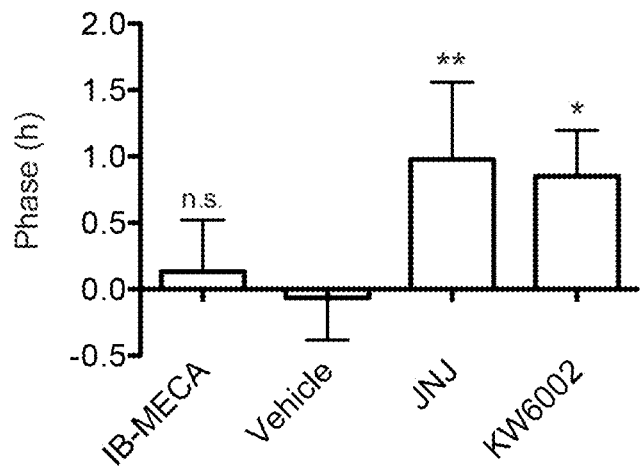
FIGS. 9A-9C are graphs that demonstrate that circadian behavioural assays show efficacy of A1/A2A dual antagonists at modifying circadian rhythms.
Figure 9B:
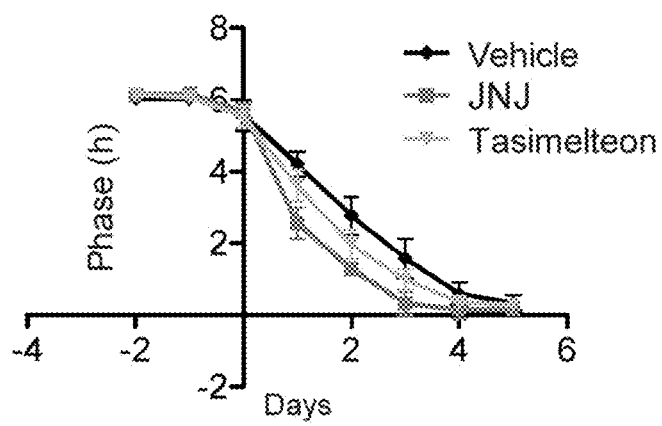
Figure 9C:
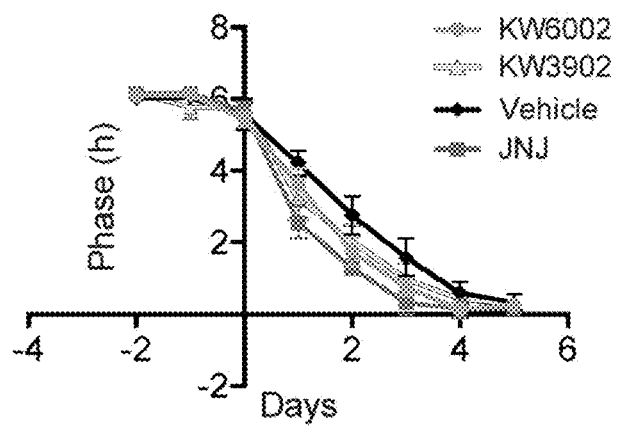

FIGS. 9A to 9C—demonstrate that circadian behavioural assays show efficacy of A1/A2A dual antagonists at modifying circadian rhythms.

FIG. 9A—this plots the phase shifts, which were measured by the difference between the two measures of onset (pre and post injection of relevant agent) JNJ40255293 (A1/A2A antagonist) causes the largest phase shifts compared with either caffeine, KW6002 or the agonist IB-MECA.

FIG. 9B—demonstrates that JNJ40255293 is more efficient at re-entrainment than current standard of care (Hetlioz).

FIG. 9C—demonstrates that JNJ40255293 is more efficient than either a specific A2A antagonist KW6002 or a specific A1 antagonist KW3902.

Figure 10A:
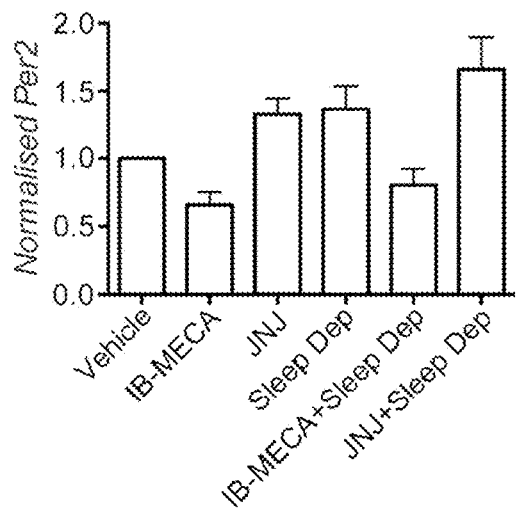
FIG. 10A is a graph that demonstrates that sleep deprivation paradoxically increases Per2 expression within the cortex.
Figure 10B:
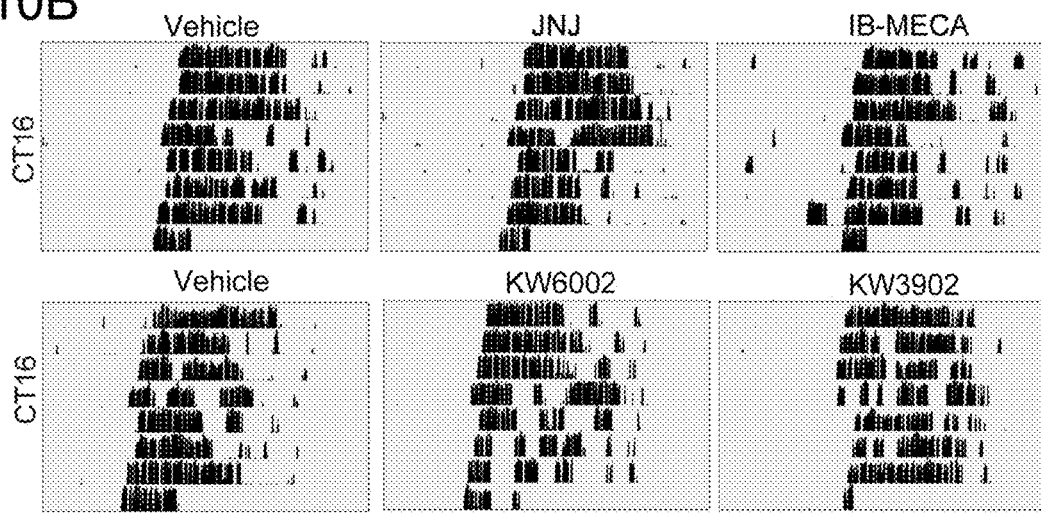
FIG. 10B shows individual actograms which support the data shown in FIGS. 5A to 5H. The various agents applied to the animals are labelled.
Figure 10C:
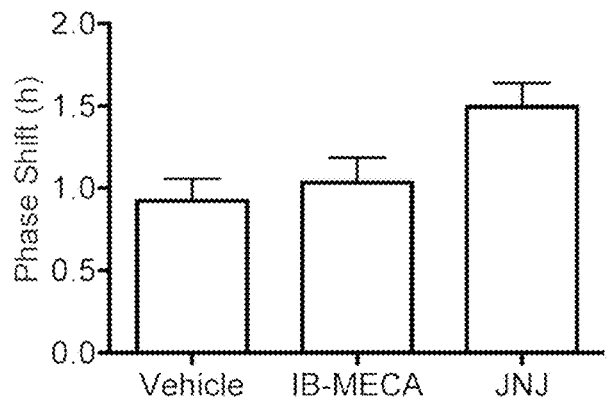
FIG. 10C is a graph that demonstrates that the $A_1/A_{2A}$ antagonist JNJ40255293 also enhances phase-shifts in response to light at CT16, unlike the non-specific agonist IB-MECA.

FIGS. 10A-10C-demonstrates that adenosine signalling regulates the sensitivity of the circadian clock to light.

FIG. 10A—demonstrates that sleep deprivation paradoxically increases Per2 expression within the cortex.

FIG. 10B—these are individual actograms which support the data shown in FIGS. 5A to H. The various agents applied to the animals are labelled.

FIG. 10C—this demonstrates that the $A_1/A_{2A}$ antagonist JNJ40255293 also enhances phase-shifts in response to light at CT16, unlike the non-specific agonist IB-MECA.

EXAMPLES

Materials and Methods
Animal Studies

Animals were housed under a reversed 12:12 LD cycle (400 lux from white LED lamps) with food and water ad libitum. For phase-shifting studies, C57Bl/6 mice were maintained on running wheels in light tight chambers on a 12:12 LD cycle (400 lux from white LED lamps) and injected with drug at the indicated time points. The drugs were formulated in a vehicle consisting of 5% Koliphor-HS15 (Sigma-Aldrich, UK) 5% Cyclodextran (Sigma-Aldrich, UK) in 0.9% saline. This vehicle was warmed to 37° C. and the indicated drugs kept at a 100× stock in DMSO and mixed at the appropriate concentration to be administered at approximately 300 ul intraperitoneal injection (n=6 to 10). Where the time point of injection was in the dark, the procedure was conducted under dim red light. Where measuring phase-shifting, the mice were then placed in DD and allowed to free run for 14 days in DD, running wheel activity data was collected and analysed on Clocklab (Actimetrics, Wilmette, IL). For jet-lag studies, mice were maintained on running wheels in light tight chambers on a 12:12 LD cycle (400 lux from white LED lamps) and injected with drugs as above at ZT6 and the LD cycle was shifted 6 hours in advance. The onset of activity on each day was used to measure phase relative to the LD cycle.

Tissue Collection

Animals were sacrificed under dim red light by cervical dislocation at 30, 60 and 120 minutes after the onset of the light pulse. The eyes were immediately removed to prevent any photic stimulation to the SCN. Sham-treated mice not given a light pulse were dissected at each time point. Brains were removed and placed into a brain matrix (Kent Scientific, Torrington CT, USA). All procedures were performed in accordance with the UK Home Office Animals (Scientific Procedures) Act 1986 and the University of Oxford's Policy on the Use of Animals in Scientific Research. (PPL 70/6382 and 30/2812). Animals were sacrificed via Schedule 1 methods in accordance with the UK Home Office Animals (Scientific Procedures) Act 1986.

SCN Tissue Collection: Animals were housed under a 12:12 LD cycle for 2 weeks with food and water ad libitum. Animals then received either a drug injection with a alteration in the light dark cycle as described in the experiment and at set points following drug administration were sacrificed by cervical dislocation. Sham-treated mice not given a light pulse were dissected at each time point. Brains were removed and placed into a brain matrix (Kent Scientific, Torrington CT, USA). Per2::Luc transgenic animals (as reported in Yoo et al, Proc Natl Acad Sci USA. 2004 Apr. 13; 101(15):5339-46) were obtained from Prof Joseph Takahashi, Northwestern University.

For punches for mRNA/protein analysis: A skin graft blade (Swann-Morton, Sheffield, UK) was positioned at Bregma −0.10 mm. A second blade was placed 1 mm (Bregma −1.10) caudal from the first, and a 1 mm thick brain slice was dissected. SCN punches were taken using a sample corer (1 mm internal diameter, Fine Science Tools GmbH, Heidelberg, Germany) from the brain slice (n=4), flash frozen on dry ice and stored at −80° C. prior to RNA extraction.

For SCN slice culture: The brain was gently cut into a cube preserving the integrity of the SCN and cut into 200 uM slices in ice-cold oxygenated Hanks Balanced Salt Solution containing 100 nM MK801 (Sigma-Aldrich). The SCN was microdissected and transferred to membrane filter (Millicell Cell Culture Insert, 30 mm, hydrophilic PTFE, 0.4 µm, Millipore) and cultured in 300 uL DMEM prepared as detailed in the Per2::Luc Assay.

Phase Shifting: C57Bl/6 male mice (80 days or older) were maintained on running wheels in light tight chambers on a 12:12 LD cycle (100 lux from white LED lamps) on stable entrainment, were released in complete darkness. At set times as indicated in the experiments, the animals received an intraperitoneal injection (300 ul) of drug constituted in sterile saline with 5% Cyclodextrin (Sigma-Aldrich) and 5% Koliphor (Sigma-Aldrich) and then allowed to free run in DD, running wheel activity data were collected and analysed on Clocklab (Actimetrics, Wilmette, IL).

Re-entrainment: C57B/6 male mice (80 days or older) were maintained on running wheels in light tight chambers on a 12:12 LD cycle (100 lux from white LED lamps) and injected with drugs as above at ZT6. The LD cycle was immediately advanced by 6 h. Onset of activity on each day was used to measure phase relative to the LD cycle, data analysed on Clocklab.

RNA Extraction and Sample Preparation

Total RNA was extracted using the microRNeasy column method (Qiagen, Hilden, Germany). Quality and quantity of RNA were measured using an Agilent Bioanalyzer and a Nanodrop1000 (Thermo Fisher Scientific, Waltham, MA USA), respectively.

Quantitative PCR (qPCR)

RNA samples were prepared as described for microarray hybridisation. cDNA was synthesized with a qScript cDNA synthesis kit (Quanta Biosciences, Gaithersburg, MD), and quantitative PCR (qPCR) was conducted with Sybr green I and an SDS7700 thermal cycler (Applied Biosystems, Foster City, CA). Relative quantification of transcript levels was done as described previously (Peirson et al., Nucleic Acids Res. 2003 Jul. 15; 31(14):e73.). The geometric mean of a minimum of three housekeeping genes was used for normalization (Gapdh, ActB, GusB and Rps9 for example).

Primer sequences below and from Jagannath et al., Cell. 2013 Aug. 29; 154(5):1100-11.

TABLE 1

Primer Sequences (SEQ ID NOS: 1-6)

| Adora1 For | TGCCAGCTTTGGTGACCTTG |
| Adora1 Rev | GCCTGGAAAGCTGAGATGGA |

TABLE 1-continued

Primer Sequences (SEQ ID NOS: 1-6)

| Adora2a For | GGACTGTGACATGGAGCAGG |
| Adora2a Rev | TTCTGGCAGCAGCATCATGG |
| Adora3 For | TCGCTGTGGACCGATACTTG |
| Adora3 Rev | AGAGCCACATGACTGGAAGG |

RNAi siRNA sequences are as follows; Non-targeting siRNA: 5' CUUACGCUGAGUACUUCGA 3'. SEQ ID NO: 17

TABLE 2 siRNA sequences: (SEQ ID NOS: 7-16)

| ADORA3 | NM_000677 | GGUCACCACUCACAGAAGA |
| ADORA3 | NM_000677 | CUACUUUAAUGGUGAGGUA |
| ADORA1 | NM_001048230 | GGUAGGUGCUGGCCUCAAA |
| ADORA1 | NM_001048230 | GGAGUCUGCUUGUCUUAGA |
| ADORA1 | NM_001048230 | CAAGAUCCCUCUCCGGUAC |
| ADORA2B | NM_000676 | UGAGCUACAUGGUAUAUUU |
| ADORA2B | NM_000676 | GGGAUGGAACCACGAAUGA |
| ADORA2B | NM_000676 | GAUGGAACCACGAAUGAAA |
| ADORA2A | NM_000675 | GAACGUCACCAACUACUUU |
| ADORA2A | NM_000675 | CAUGCUGGGUGUCUAUUUG |

Cell Lines and Culture

Cells from the U2OS (HTB-96) line were obtained, tested and identified. The cells were cultured in T-75 flasks, in Dulbecco's modified Eagle medium (DMEM) supplemented with 10% foetal bovine serum (FBS) and 1% penicillin-streptomycin (P/S) at 37° C. in a humidified atmosphere at 5% $CO_2$. The cells were subcultured every 2 to 4 days in a 1:2 to 1:6 ratio, in accordance with the ATCC recommendations. The cells were counted using a haemocytometer, and their viability in a culture was maintained at above 95%, measured with a Presto Blue exclusion assay according to the manufacturer's specifications. Cells were transfected with siRNAs (typically at 50 nM concentrations, sequences as previously listed), the CRE::Luc (pGL4.29[luc2P/CRE/Hygro] Vector, encoding Luc2P luciferin under the control of a strong cAMP response element (CRE) promoter containing 3 CRE elements within its sequence; Promega) reporter vector or cAMP-GLOSensor plasmid (Promega) as per manufacturer's instructions using either Lipofectamine RNAimax (Invitrogen) or Lipofectamine3000 (Invitrogen).

Per2::Luc Cell Based Circadian Assays

U2OS cells stably transfected with a Per2::Luc reporter were cultured in DMEM supplemented with 10% FBS. For siRNA- and drug-based experiments, cells were seeded at 5,000 per well into white 384 well plates and transfected with 20 nM siRNA the next day. 2 days later, the cells were synchronized with 100 nM dexamethasone and the medium was replaced with phenol-red free DMEM supplemented with B-27 and 100 M luciferin potassium salt, requisite drugs formulated in DMSO as a 1000× stock was added, and then sealed. Per2::Luc rhythms were recorded from a BMG Labtech Fluostar Omega plate reader maintained at 36° C. and readings taken from each well every hour. Data were then analysed using either Multicycle or Brass rhythm analysis software.

Per2::Luc Circadian Assays:

Period2::Luciferase (Per2::Luc) stable U2OS transfects were cultured, as described above. A Greiner Bio-One 384 Well Plate (Polystyrene, F-bottom), was then seeded at 6000 cells per 50 µl well. Following a 24 hour period, the cells were treated with 0.1% dexamethasone, a glucocorticoid hormone analogue known to reset intracellular circadian rhythms, for 1 hour. Subsequently, the dexamethasone-containing medium was removed, the cells were washed with PBS and luciferin and test drug containing medium was added. The cells were then assayed for luminescence over a period of 96 hours in the BMG FLUOstar OPTIMA Microplate Reader to observe the periodicity and amplitude of the luminescence values.

STAR-PROM Assay

This was conducted as previously reported in Gerber et al., Cell. 2013 Jan. 31; 152(3):492-503. Briefly, U2OS cells were cultured in 6-well plates and transfected with 1 ug of the STAR-PROM plasmid library (library structure as in above reference). RNA was extracted at set time points and sequenced for the barcoded luciferase constructs and analysed with Galaxy (https://use.galaxy.org).

CRE-Luc Vector Transfection

At 60-80% confluence and >90% viability, the U2OS cells in the T-75 flask were washed twice with 6 ml phosphate-buffered saline (PBS) and subsequently treated with 4 ml of TrypLE™ Express trypsin replacement solution for 10 minutes. A Greiner Bio-One 96 Well Plate (white, TC treated), was then seeded at 8000 cells per well. Following 24 hours, the cells were transfected at 50-70% confluency with CRE-luc Vector generated in-house with Viafect transfection reagent at 1:4 ratio (100 ng DNA/well) following manufacturers recommendations.

CRE-Luc Luciferase Assay 24 hours after transfection, the medium in the 96 well plate was changed to a serum-free medium with 1 mM luciferin. The cells were then incubated in serum starvation conditions for 6-8 hours, this was optimised to yield the greatest signal strength and lowest noise when assayed with forskolin control. Following the incubation period, the CRE-Luc U2OS cells were treated with the appropriate drug and their luminescence values were measured after 6 hours in the BMG FLUOstar OPTIMA Microplate Reader. For comparative experiments, drug concentrations of 10 µM were used as they were found to be optimal for keeping cell toxicity below 5%, measured with the Presto Blue exclusion assay. Unless stated otherwise, forskolin was used as a positive control, and 1% DMSO was used as a negative control.

cAMP GloSensor Assay

The GloSensor™ cAMP Assay (Promega) was used for detecting changes in the intracellular levels of cAMP. Initially, a Greiner Bio-One 96 Well Plate (white, TC treated) was seeded at 8000 cells per 100 µl well, as described above. After 24 hours, the cells were transfected with the pGloSensor™ cAMP Plasmid using the Viafect transfection reagent as above. Between 24 and 48 hours later, allowing for the accumulation of the biosensor, the medium in the 96 well plate was changed to C02-Independent Medium supplemented with GlutaMAX™ (Life Technologies), 10% fetal bovine serum and 2% GloSensor™ cAMP Reagent. The plate was then stood for 2 hours at room temperature to equilibrate. Following the incubation period, the cells were treated with relevant drugs and their luminescence values were measured after 20 minutes in the BMG FLUOstar OPTIMA Microplate Reader, with forskolin as a positive control, and DMSO as a negative control.

Statistics

Statistical analyses and dose-response curves were performed by the use of Graph Pad Prism 5.0 software. Two-tailed Student's t-test was used to calculate the P values for unpaired, homoscedastic comparisons, with the P values <0.05 being considered statistically significant. *P<0.05, P<0.01, *P<0.001. ANOVAs were used to perform multiple comparisons. Error bars on the graphs indicate one standard error of the mean (SEM). In addition, all results are presented in the form of average±SEM.

Results and Discussion

Adenosine Receptor Agonists Activate Gene Clock Expression in U2OS Cells

U2OS cell lines treated with the adenosine receptor agonist IB-MECA show increases in period and amplitude of the cellular clock as reported by the Per2::Luciferase construct (FIG. 1A). In addition to a dose dependent increase in circadian period, IB-MECA caused a concurrent increase in the second messenger cyclic AMP (cAMP) levels (FIG. 1B) and activation of the cAMP response element-binding factor (CREB) as indicated by the CRE::Luc reporter construct (FIG. 1C). These experiments were repeated with other adenosine receptor agonists (1-5 as detailed in FIGS. 1D and E) and similar increases in cAMP levels and CRE::Luc were observed (FIGS. 1D and 1E). IB-MECA induced dose-dependent period length increases (FIG. 1F) resulting rapid expression of the clock genes Per1/2 expression (FIG. 1H). Similar increases in period length were observed with BAY606583 (FIG. 1G).

Adenosine Receptor Agonists Phase Shift Circadian Rhythms and Modulate the Effect of Light on the Central Circadian Clock C57Bl/6 male mice (80+ days) were housed in a 12 h-light 12 h-dark cycle (400 lux). Stable entrainment was indicated by the onset of activity (green) during the dark part of the cycle (grey). Animals were administered Vehicle (FIG. 2A) or IB-MECA, 1 mg/kg intra-peritonially (FIG. 2B) followed by a light pulse at ZT22 (indicated by the arrow, 22 h after the onset of light). The results shown in FIG. 2A demonstrate that a light pulse at CT22 normally induced a phase advance, indicated by the advance in activity (point of intersection of the two black lines is advanced) after the animals were housed in constant dark (grey). Results shown in FIG. 2B show that the phase advance was lost when IB-MECA was administered (point of intersection of the black lines remains at the day at which the animals were released into DD, indicating no phase shift). Data summarized in (FIG. 2C). Results shown in FIG. 2D demonstrate that in the absence of a light pulse, IB-MECA elicited a phase delay when administered at CT22, whilst the vehicle and antagonist induced no significant change in phase.

Adenosine Receptor Antagonists Modulate Circadian Rhythms and Clock Gene Expression in U2OS Cells.

As the adenosine receptor agonists activated the circadian gene Per1/2 expression, we hypothesised these effects were as a result of adenosine receptor activation. By extension we anticipated these effects to be blocked by the pan-adenosine receptor antagonist CGS15943(9-chloro-2-(furan-2-yl)-[1,2,4]triazolo[1,5-c]quinazolin-5-amine). However, multiple adenosine receptor antagonists Istradefylline, JNJ40255293, MRS1220 and ZM241385 surprisingly and unexpectedly increased circadian period length in a dose dependent manner (FIGS. 3A-3G)). FIG. 3A shows that period lengthening was observed in Per2::Luc U2OS cells treated with JNJ40255293 (the time of application being indicated by the arrow and doses as indicated). As the cAMP could have increased as a consequence of antagonising A1 receptor (Gi coupled), the alterations in cAMP as a consequence of A1 receptor blockade in U2OS cells was evaluated. Results shown in FIGS. 3B and 3C demonstrate that none of the adenosine receptor antagonists increased the intracellular cAMP or CREB activation in U2OS cells. However, dose responsive period lengthening was observed as shown in FIGS. 3D-H in JNJ40255293, istradefylline, MRS1220 and ZM241385-treated U2OS cells respectively. In order to verify that the observed effects were due to action on adenosine receptors, the $A_1$, $A_{2A}$, $A_{2B}$ adenosine receptors in U2OS cells were knocked down using siRNA and the effects of the antagonists were evaluated. FIG. 3H, shows the effects of the antagonists were was abolished confirming that the observed effect on period is indeed through action on adenosine receptors.

The absence of the CRE::Luc response indicates an alternative transcriptional pathway culminating in clock gene expression. To identify this pathway, STAR-PROM screening was conducted (as described in Gerber et al., 2013, Cell and in collaboration with Prof. Ulrich Schibler, Geneva). This system comprises a library of synthetic promoter elements driving luciferase expression and can be used to identify new transcriptional elements activated by drugs or treatments. JNJ40255293 activated the expression of several reporter constructs as highlighted by the grey box in FIG. 3I.

Results shown in FIGS. 3J and 3K show that Per1 and Per2 mRNA levels respectively were elevated after JNJ40255293 application (30 uM) in U2OS cells.

Adenosine Receptor Antagonists Phase Shift Circadian Rhythms and Enhance Entrainment in a Jet-Lag Protocol C57B/6 male mice (80+ days) were housed in a 12 h-light 12 h-dark cycle (400 lux). Stable entrainment was indicated by the onset of activity (black) during the dark part of the cycle (grey). Animals were administered Vehicle (FIG. 4A) or JNJ40255293, 5 mg/kg intraperitonial injection (FIG. 4B) (indicated by the arrow, 6 h after the onset of light). JNJ40255293 induced a phase advance, indicated by the advance in activity (diagonal line) after the animals were housed in constant dark (grey). Data summarized in (C). Similarly, JNJ40255293 was administered at CT16 (circadian time 16 or 16 h after the onset of light) and resulted in a phase delay, indicating the same drug would have different effects on circadian phase at different times, similar to light (FIG. 4E). The same protocol as above was followed as for FIGS. 4A and 4B, with the exception that rather than a release of the animals into constant dark after drug administrations, the light-dark cycle was advanced 6 h to simulate an eastward flight and an advance of 6 time zones. The vehicle treated animals (FIG. 4E) advanced their activity gradually each day, and in contrast the JNJ40255293 treated animals (FIG. 4F) shifted rapidly. The results shown in FIG. 4G show enhancement of re-entrainment was observed for both JNJ40255293 (FIG. 4G). Results shown in FIGS. 4H and 4I show that Per1 and Per2 mRNA levels respectively were elevated within the SCN after administration of JNJ40255293 in the periphery (intra-peritonially), indicating the drug's central effect. Results shown in FIGS. 4J and 4K are from experiments were animals were housed in constant dark and at CT16 or 4 hours after subjective dusk received either vehicle or 5 mg/kg JNJ40255293 or 1 mg/kg IB-MECA (data not shown) and onsets of activity measured. Phase shifts were measured by the difference between the two measures of onset (pre and post injection) and plotted. JNJ40255293 at this time causes a phase delay.

Adenosine Receptor Antagonists/Inverse Agonists Regulate Cellular Clocks Via a Novel Signalling Pathway.

FIGS. 5A-5F and 6A to 6F detail the effect of adenosine receptor antagonists on the cellular clock. Whilst we expected the opposite from antagonists than the agonists, we were surprised to find that antagonists of $A_1/A_{2A}$ receptors such as JNJ40255293 produced large dose-dependent increases in period length. We observed little if any increases in cAMP (50% increase at 30 uM), certainly not to the levels required to elicit changes in circadian period. Correspondingly, we saw no changes in CREB phosphorylation or signal for CRE::Luc reporters, but observed significantly increased Per1/2 transcription at 4 h post-drug treatment (thus with a significantly different time course as the agonists) and changes in period length. These findings implicate a novel CREB-independent transcriptional axis downstream of adenosine receptors that causes a delayed induction Per1/2 transcription. Mixed $A_1/A_{2A}$ antagonists achieved this effect (e.g. JNJ40255293) but neither $A_1$ specific not $A_{2A}/A_{2B}$ specific antagonists were able to replicate this effect. In order to identify the novel transcriptional axis downstream of $A_1/A_{2A}$ antagonism that converged on the clock, we employed the unbiased transcription factor screening approach BC-STARPROM/30 uM JNJ40255293 significantly increased the reporter signal from 8 clones, 7 of which were predicted to contain Fos-related transcription factor binding site. We isolated clone3, which we found responded to a panel of different antagonists including JNJ40255293. The DNA sequence containing the promoter region of clone 3 was used to pull down protein binding partners from a nuclear extract of cells treated with JNJ40255293 and the isolated proteins sequenced using mass spectrometry. A few transcription factors were enriched in the CGS-treated samples, including JunD and Fosl2. Correspondingly, siRNA-mediated silencing of Fos significantly reduced the response of clone3 to CGS15943. Analysis of the Per1 and Per2 promoters revealed conserved Fos:Jun binding site within their promoters (data not shown).

FIG. 5: (A) JNJ40255293 does not elevate cAMP levels in U2OS cells or (B) increase phosphorylation of CREB, in contrast to the positive controls Forskolin of IB-MECA. (C) Robust increases in Per1 and Per2 mRNA are seen after treatment with 10 uM JNJ40255293, leading to (D) increases in period length in Bmal1::Luc reporter U2OS cells which revert to normal rhythms after washout of drug. (E) Dose-responsive increases in period length are observed. FIGS. 6A to 6F show that multiple adenosine receptor antagonists perturb circadian rhythms in U2OS cells in a CREB-independent manner.

The STAR-PROM Approach Reveals a Novel Signalling Pathway Downstream of Adenosine Receptor Inhibition that Converges on the Circadian Clock.

This is demonstrated in FIGS. 7A to 7E and 3. FIG. 7C shows the activity of Seq3 after knockdown of Fos (siFos) when compared with a non-targeting siRNA (siNT) and induction by JNJ40255293 compared with DMSO. This demonstrates an alternate pathway leading from the mixed antagonists to Per1/2. The specific expression of one reporter that contains the same transcriptional binding element as found in Per2. The upper line represents the induction of expression of the clone on treatment with JNJ40255293 and the lower lines represent the same after silencing of the candidate transcription factor AP1 (consisting of the subunits Fos and Jun). These data confirm that AP1 is responsible for the transcription of Per1/2 after treatment with JNJ40255293.

The SCN Expresses Adenosine Receptors and is Sensitive to Adenosine Receptor Antagonists/Inverse Agonists.

We then extended our work to the central pacemaker and found that JNJ40255293 increased period length in isolated Per2::Luc SCN slice cultures. Intraperitoneal injections of JNJ40255293 increased Per1 and Per2 expression. FIG. 8A to C depicts these results.

Circadian Behavioural Assays Show Efficacy of A1/A2A Dual Antagonists at Modifying Circadian Rhythms.

FIG. 9 A to C show graphs that represent the speed of entrainment of mice treated a single intraperitoneal injection of the drugs JNJ40255293 (5 mg/kg), Tasimelteon (5 mg/kg) KW6002 (1 mg/kg) and KW3902 (1 mg/kg). The light dark cycle was advanced by six hours after the injection at ZT6 and the phase of onset of activity (marking circadian time in the animals) was plotted. Vehicle treated animals typically took 5-6 days to return to baseline, while JNJ40255293 clearly advanced entrainment more potently than Tasimelteon, KW6002 (specific $A_{2A}$ antagonist) or KW3902 (specific $A_1$ antagonist).

Adenosine Signalling Regulates the Sensitivity of the Circadian Clock to Light.

We investigated the physiological relevance of our findings to the sleep axis. We predicted that sleep deprivation would increase levels of extracellular adenosine and that this would decrease clock gene expression. We found that as predicted, sleep deprivation decreases Per1/2 expression within the SCN, consistent with increased adenosine-A signalling and that this decrease was reversed by administration of JNJ40255293 and mimicked by administration of an $A_1$ agonist. An $A_{2A}$ specific agonist CGS21680 had the opposite effect and increased Per1/2 expression (data not shown). We also found as previously reported, that sleep deprivation increased Per1/2 within the cortex, and that this increase was more due to the stress-glucocorticoid signalling axis as administration of mifepristone blunted this response (data not shown). The implication of these findings is that adenosine levels (presumably influenced by sleep history) can influence circadian responses. We tested this in the context of circadian-phase shifts to light. We hypothesised that $A_1$ antagonists would enhance the effects of light, whereas A1 agonists would inhibit the phase-shifting effect of light. This is indeed what we found, that we were able to alter the depths of the two arms of the light PRC by modulating adenosine signalling. The implications of this finding could explain the different light PRCs in nocturnal versus diurnal animals The data in FIG. 10 A to 10 C shows that sleep deprivation paradoxically increases Per2 expression within the cortex. Individual actograms (10B) supports the assertion that adenosine signalling regulates the sensitivity of the circadian clock to light. 10C shows that the $A_1/A_{2A}$ antagonist JNJ40255293 also enhances phase-shifts in response to light at CT16, unlike the non-specific agonist IB-MECA.

The experiments detailed in FIGS. 1-10 describe the effect of adenosine receptor modulators and adenosine signalling on circadian clock function. Through both canonical (CREB-based) and novel pathways, drugs targeting the adenosine receptor system activate clock gene expression and provide a zeitgeber or time-giving message to the circadian clock. This can be used to reset, i.e. to advance or delay the phase and period of the circadian clock in vitro and also in vivo. These results support the use of adenosine receptor modulators as chronomodulatory compounds, particularly where at least two adenosine receptors are modulated in tandem.

All documents mentioned herein are incorporated by reference.

Other embodiments are intentionally within the scope of the invention as defined by the appended claims.

What is claimed is:

1. A method of adjusting a circadian rhythm in a subject with a circadian rhythm disorder comprising providing a subject with a pharmaceutical composition comprising a selective adenosine receptor antagonist which antagonises both the $A_1$ and $A_{2A}$ receptors, in an amount sufficient to adjust a circadian rhythm, wherein said subject is anophthalmic.

2. The method of claim 1 wherein the subject has a circadian rhythm disorder selected from jet-lag disorder, rapid time zone change syndrome, delayed sleep-phase disorder, advanced sleep-phase disorder, irregular sleep wake rhythmic disorder, non-24-hour sleep wake disorder, shift-work disorder, or disruptive circadian rhythms.

3. The method of claim 1 wherein the subject has non-24-hour sleep wake disorder.

4. The method of claim 1 wherein said selective adenosine receptor antagonist which antagonises both the $A_1$ and $A_{2A}$ receptors is selected from 2-amino-8-[2-(4-morpholinyl) ethoxy]-4-phenyl-5H-indeno[1,2-d]pyrimidin-5-one, (JNJ40255293) or 2-butyl-9-methyl-8-(triazol-2-yl)purin-6-amine (ST-1535), or a salt thereof.

5. The method of claim 1 wherein said pharmaceutical composition is formulated as dosage forms for oral, parenteral, intravenous, subcutaneous, intradermal, intra-arterial, intra-cardial, rectal, nasal, topical, aerosol or vaginal administration.

6. The method of claim 1 wherein said amount is sufficient to result in entrainment of the subject to a 24 hour circadian rhythm.

7. The method of claim 1, wherein the composition is administered at Circadian Time 4 to 8, Circadian Time 6, Circadian Time 14 to 18, or Circadian Time 16.

8. The method of claim 7 wherein the composition is administered at Circadian Time 4 to 8.

9. The method of claim 1, wherein the composition results in an increase in Per1 or Per2 gene expression in a subject, and
  wherein the increase in Per1 or Per2 gene expression is observed at least 2 to 6 hours after administration to the subject, or
  wherein the increase in Per1 or Per2 gene expression is observed at least 4 hours after administration to the subject.

10. The method of claim 9, wherein the increase in Per1 or Per2 gene expression is about 10%, about 20%, about 30%, about 40%, about 50%, about 60%, about 70%, about 80%, about 90%, about 100% or more increase in expression compared to a subject that did not receive the composition.

11. A method of adjusting a circadian rhythm in an anophthalmic subject with a circadian rhythm disorder comprising providing the anophthalmic subject with a pharmaceutical composition comprising a selective adenosine receptor antagonist which antagonises both the $A_1$ and $A_{2A}$ receptors, in an amount sufficient to adjust a circadian rhythm, wherein the circadian rhythm of the anophthalmic subject with the circadian rhythm disorder is adjusted.

* * * * *

SEQUENCE LISTING

```
<160> NUMBER OF SEQ ID NOS: 17

<210> SEQ ID NO 1
<211> LENGTH: 20
<212> TYPE: DNA
<213> ORGANISM: Homo sapiens

<400> SEQUENCE: 1
tgccagcttt ggtgaccttg                                        20

<210> SEQ ID NO 2
<211> LENGTH: 20
<212> TYPE: DNA
<213> ORGANISM: Homo sapiens

<400> SEQUENCE: 2
gcctggaaag ctgagatgga                                        20

<210> SEQ ID NO 3
<211> LENGTH: 20
<212> TYPE: DNA
<213> ORGANISM: Homo sapiens

<400> SEQUENCE: 3
ggactgtgac atggagcagg                                        20
```

```
<210> SEQ ID NO 4
<211> LENGTH: 20
<212> TYPE: DNA
<213> ORGANISM: Homo sapiens

<400> SEQUENCE: 4
ttctggcagc agcatcatgg                                                   20

<210> SEQ ID NO 5
<211> LENGTH: 20
<212> TYPE: DNA
<213> ORGANISM: Homo sapiens

<400> SEQUENCE: 5
tcgctgtgga ccgatacttg                                                   20

<210> SEQ ID NO 6
<211> LENGTH: 20
<212> TYPE: DNA
<213> ORGANISM: Homo sapiens

<400> SEQUENCE: 6
agagccacat gactggaagg                                                   20

<210> SEQ ID NO 7
<211> LENGTH: 19
<212> TYPE: RNA
<213> ORGANISM: Homo sapiens

<400> SEQUENCE: 7
ggucaccacu cacagaaga                                                    19

<210> SEQ ID NO 8
<211> LENGTH: 19
<212> TYPE: RNA
<213> ORGANISM: Homo sapiens

<400> SEQUENCE: 8
cuacuuuaau ggugaggua                                                    19

<210> SEQ ID NO 9
<211> LENGTH: 19
<212> TYPE: RNA
<213> ORGANISM: Homo sapiens

<400> SEQUENCE: 9
gguaggugcu ggccucaaa                                                    19

<210> SEQ ID NO 10
<211> LENGTH: 19
<212> TYPE: RNA
<213> ORGANISM: Homo sapiens

<400> SEQUENCE: 10
ggagucugcu ugucuuaga                                                    19

<210> SEQ ID NO 11
<211> LENGTH: 19
<212> TYPE: RNA
<213> ORGANISM: Homo sapiens

<400> SEQUENCE: 11
```

```
caagaucccu cuccgguac                                               19

<210> SEQ ID NO 12
<211> LENGTH: 19
<212> TYPE: RNA
<213> ORGANISM: Homo sapiens

<400> SEQUENCE: 12
ugagcuacau gguauauuu                                               19

<210> SEQ ID NO 13
<211> LENGTH: 19
<212> TYPE: RNA
<213> ORGANISM: Homo sapiens

<400> SEQUENCE: 13
gggauggaac cacgaauga                                               19

<210> SEQ ID NO 14
<211> LENGTH: 19
<212> TYPE: RNA
<213> ORGANISM: Homo sapiens

<400> SEQUENCE: 14
gauggaacca cgaaugaaa                                               19

<210> SEQ ID NO 15
<211> LENGTH: 19
<212> TYPE: RNA
<213> ORGANISM: Homo sapiens

<400> SEQUENCE: 15
gaacgucacc aacuacuuu                                               19

<210> SEQ ID NO 16
<211> LENGTH: 19
<212> TYPE: RNA
<213> ORGANISM: Homo sapiens

<400> SEQUENCE: 16
caugcugggu gucuauuug                                               19

<210> SEQ ID NO 17
<211> LENGTH: 19
<212> TYPE: RNA
<213> ORGANISM: Homo sapiens

<400> SEQUENCE: 17
cuuacgcuga guacuucga                                               19
```